United States Patent
D'Arcangelo et al.

(10) Patent No.: US 8,435,231 B2
(45) Date of Patent: May 7, 2013

(54) POSITIONING DEVICE FOR DEPLOYING AT LEAST ONE LOCKING PORTION OF AN ANASTOMOTIC DEVICE AND METHOD FOR CARRYING OUT ANASTOMOSIS IN TRACTS OF THE DIGESTIVE TUBE

(75) Inventors: Michele D'Arcangelo, Via Benedetto Croce (IT); Jesse J. Kuhns, Cincinnati, OH (US); Alessandro Pastorelli, Via Francessco (IT); Federico Bilotti, Via Bernina (IT); Roberto Tacchino, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 723 days.

(21) Appl. No.: 12/159,003

(22) PCT Filed: Jan. 11, 2007

(86) PCT No.: PCT/EP2007/000196
§ 371 (c)(1),
(2), (4) Date: Dec. 7, 2009

(87) PCT Pub. No.: WO2007/080112
PCT Pub. Date: Jul. 19, 2007

(65) Prior Publication Data
US 2010/0069933 A1    Mar. 18, 2010

(30) Foreign Application Priority Data

Jan. 16, 2006  (IT) .............................. MI2006A0060

(51) Int. Cl.
*A61B 17/00*    (2006.01)

(52) U.S. Cl.
USPC ............................................................ 606/1

(58) Field of Classification Search ........................ None
See application file for complete search history.

(56) References Cited

U.S. PATENT DOCUMENTS

| 2001/0016749 A1 | 8/2001 | Blatter et al. |
| 2004/0097994 A1 | 5/2004 | Blatter |
| 2005/0216043 A1 | 9/2005 | Blatter et al. |

*Primary Examiner* — Melanie Tyson
*Assistant Examiner* — Son Dang

(57) ABSTRACT

A positioning device for deploying at least one locking portion (20) of an anastomotic device (10) for drawing together a first tissue portion (12) and a second tissue portion (14) to be connected by means of anastomosis is suitable for sliding along a guide means comprising at least one guide wire (A, B) and comprises an elongated structure (50). A head (52) of the positioning device is suitable to be interference-inserted on a distal end of the elongated structure (50). The head (52) comprises elastic tabs (54) extending from a proximal end of the head and at least one channel (56) suitable for receiving a guide wire. The head (52) comprises a distal end defining a thrust surface (58) for a locking portion (20) of the anastomotic device (10).

6 Claims, 38 Drawing Sheets

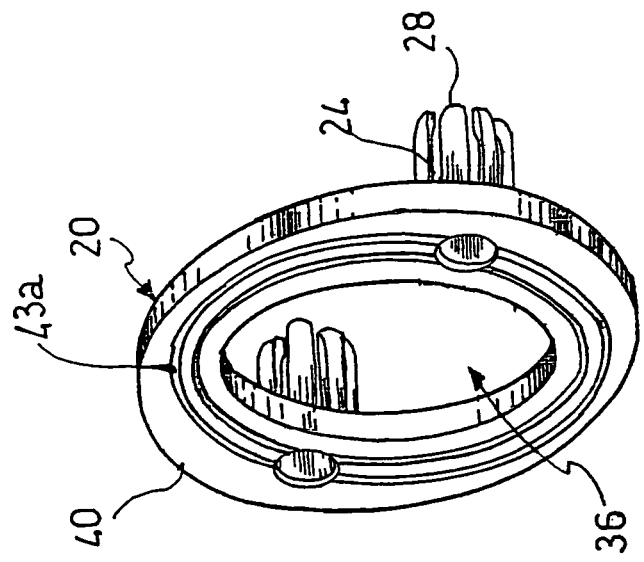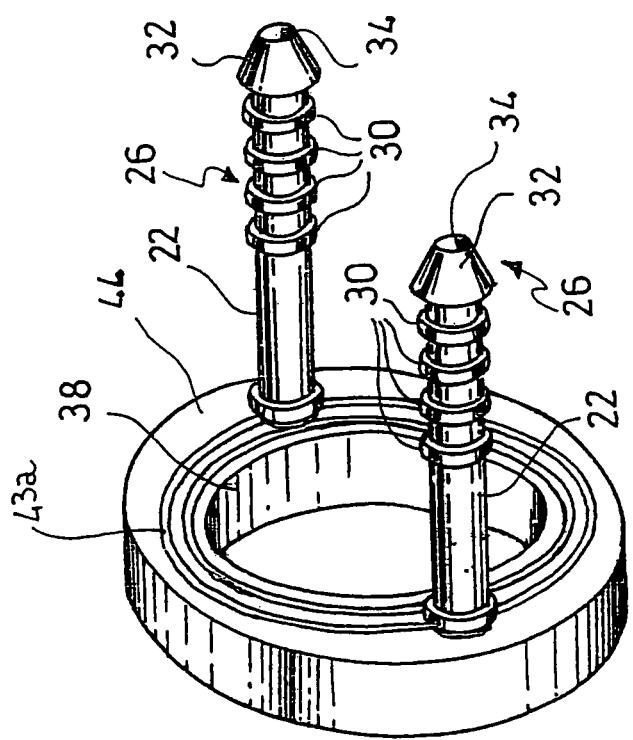
FIG. 37

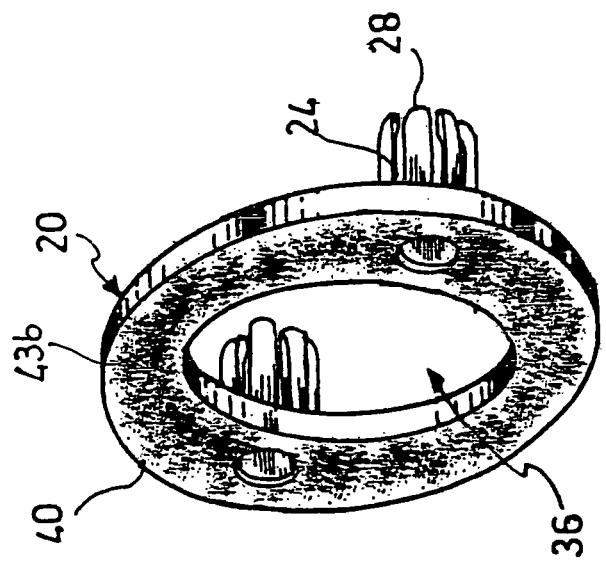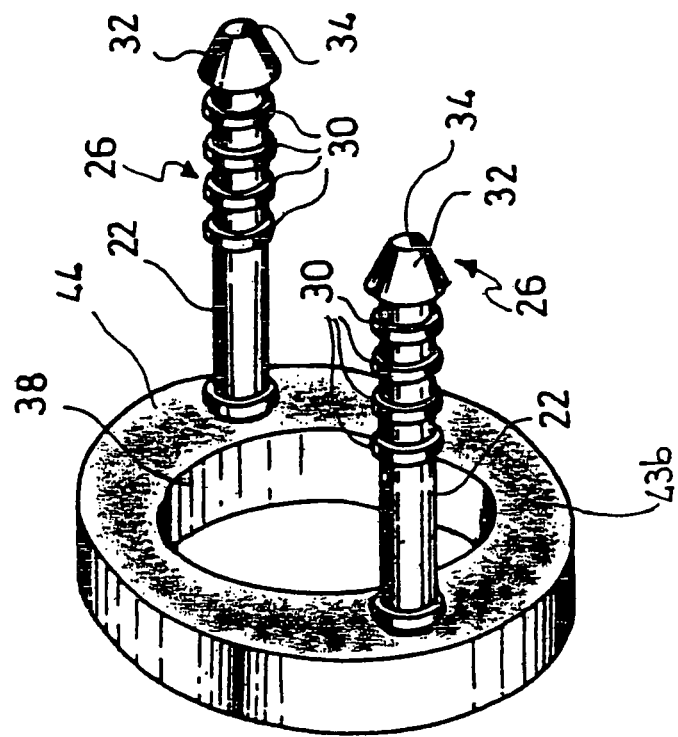
FIG. 38

POSITIONING DEVICE FOR DEPLOYING AT LEAST ONE LOCKING PORTION OF AN ANASTOMOTIC DEVICE AND METHOD FOR CARRYING OUT ANASTOMOSIS IN TRACTS OF THE DIGESTIVE TUBE

The present invention generally relates to devices to be used in methods for carrying out anastomosis in tracts of the digestive tube. In particular, these devices are suitable for performing anastomoses endoluminally, even if they can be used in partially or wholly laparoscopic techniques or in conventional surgery techniques.

In accordance with a first aspect, it is an object of the present invention a positioning device for deploying at least one locking portion of an anastomotic device. Said positioning device is particularly suitable for being applied endoluminally, such as using one or more guide wires, even though it can be used in partially or wholly laparoscopic or traditional surgery techniques.

According to a further aspect, the present invention relates to a method for carrying out anastomosis in tracts of the digestive tube. This method is also particularly suitable for being used endoluminally, even though it can be used in partially or wholly laparoscopic or traditional surgery techniques.

The known devices for carrying out anastomosis are quite invasive and need the use of positioning devices that are quite complex and bulky. Furthermore, the known devices do not allow an endoluminal, or at least partially endoluminal, approach.

As it is known, the endoluminal approach considerably minimizes the drawbacks of the conventional surgical or laparoscopic methodology. In particular, it allows minimizing the invasiveness of the procedure, thus decreasing the risks for the patient and shortening the post-operative course.

It is currently extremely difficult to utilize the endoluminal approach to perform anastomoses in tracts of the digestive tube, in particular due to the lack of equipment suitable to this aim. Consequently, the anastomoses of tracts of the digestive tube, for example to perform gastro-intestinal bypasses, are currently conducted through conventional surgical or laparoscopic techniques.

The problem addressed by the present invention is to propose devices for use in methods to perform anastomosis in tracts of the digestive tube, which allow to solve the drawbacks cited herein with reference to the prior art.

A further problem addressed by the present invention is to propose devices for use in methods to perform anastomoses in tracts of the digestive tube that are particularly suitable for endoluminal use, thus allowing to meet the increasing need to widen the utilization fields for this technique, while being also suitable for use in partially or wholly laparoscopic techniques or in conventional surgery techniques.

This problem is solved by means of a positioning device for deploying at least one locking portion of an anastomotic device in accordance with claim 1. This problem is also solved by means of a method for carrying out anastomoses in tracts of the digestive tube in accordance with claim 12.

Further characteristics and advantages of the device according to the invention will result from the description below of preferred exemplary embodiments, which are given as a non-limiting indication, with reference to the attached figures, wherein:

FIG. 37 illustrates a possible variant embodiment of an anastomotic device;

FIG. 38 illustrates a possible further variant embodiment of an anastomotic device.

Figure 1:
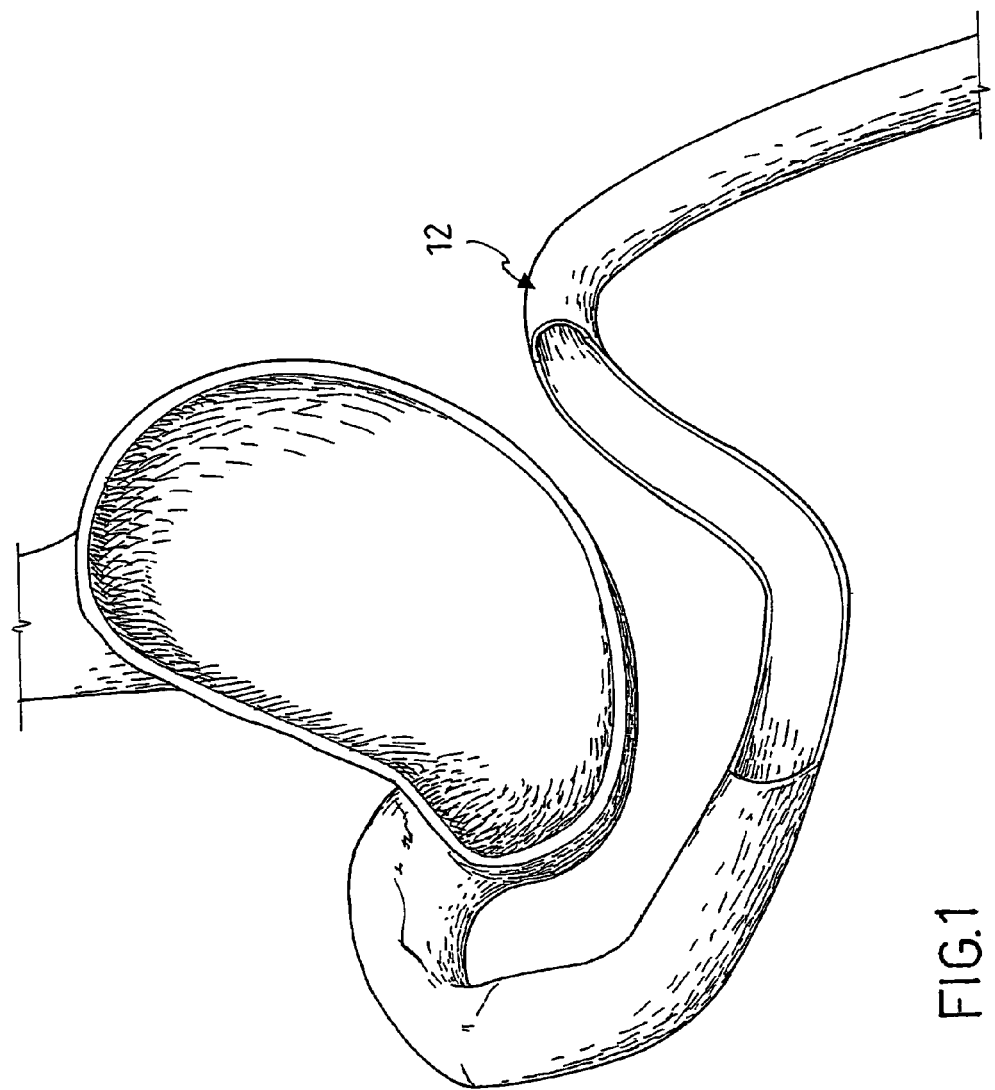
FIG. 1 illustrates a perspective view of a portion of stomach and intestine partially in section.

With reference to FIGS. 22-27 and 32-34, a positioning device according to the present invention has been illustrated with 48. The positioning device is suitable for deploying at least one locking portion 20 of an anastomotic device 10 for approximating a first tissue portion 12 and a second tissue portion 14 to be connected by means of anastomosis. An exemplary embodiment of the anastomotic device will be described below.

The positioning device is suitable to exert a thrust on the locking portion 20 in order to snap-connect the latter to an abutment portion 18 of the anastomotic device 10 which is placed opposite the first and second tissue portions.

The positioning device is advantageously suitable to slide along a guide means comprising at least one guide wire A, B and comprises an elongated structure 50.

According to a possible embodiment, the positioning device according to the present invention comprises a head 52 suitable to be interference-fitted on a distal end of the elongated structure 50. The head 52 is suitable to abut against a portion of the anastomotic device. Advantageously, the head 52 comprises elastic tabs 54 which extend from a proximal end of the same head in order to insert and hold the head onto the elongated structure.

In accordance with a possible embodiment, the head 52 comprises at least one channel 56 suitable for receiving a guide wire, such that the aforesaid positioning device is advantageously suitable for sliding along said guide means. According to a preferred exemplary embodiment as illustrated in the figures, the head 52 comprises two channels 56 which are suitable for receiving a guide wire, respectively. Advantageously, the channels 56 are placed on opposite sides of the head 52.

Advantageously, the head 52 comprises a distal end defining a thrust surface 58 for a locking portion 20 of the anastomotic device 10. Preferably, the distal end is counter-shaped relative to the locking portion 20 of the anastomotic device 10. Particularly, in the case where the locking portion comprises seats 24 with elastic tabs 28 extending away therefrom, the distal end of the head 52 comprises at least one opening 60 for receiving said elastic tabs 28.

In accordance with a possible embodiment, the elongated structure is a visualization device, such as a gastroscope. In accordance with possible embodiments, the head 52 can be applied both to a flexible structure and a rigid structure.

As will be described below in greater detail, the locking portion 20 is suitable for sliding along a guide means comprising at least one guide wire A, B and has an interaction portion with the positioning device 48 which pushes the latter along the guide wire A, B.

An example of application and operation of the positioning device 48 will be described below with reference to FIG. 22-28.

The positioning device allows adapting previously existing structures, such as visualization devices (gastroscopes), in particular to the purpose of carrying out an endoluminal technique to perform anastomosis of tracts of the digestive tube.

The elongated structure can however be done both via a flexible structure, and via a rigid structure, in order to exert a higher bias on the anastomotic device, and via a "stiffening" structure, i.e. a flexible structure suitable for becoming rigid.

The positioning device according to the present invention is easy and efficient and, by being able to slide on guide wires, it allows for a correct positioning of the two portions of the anastomotic device.

Figure 30:
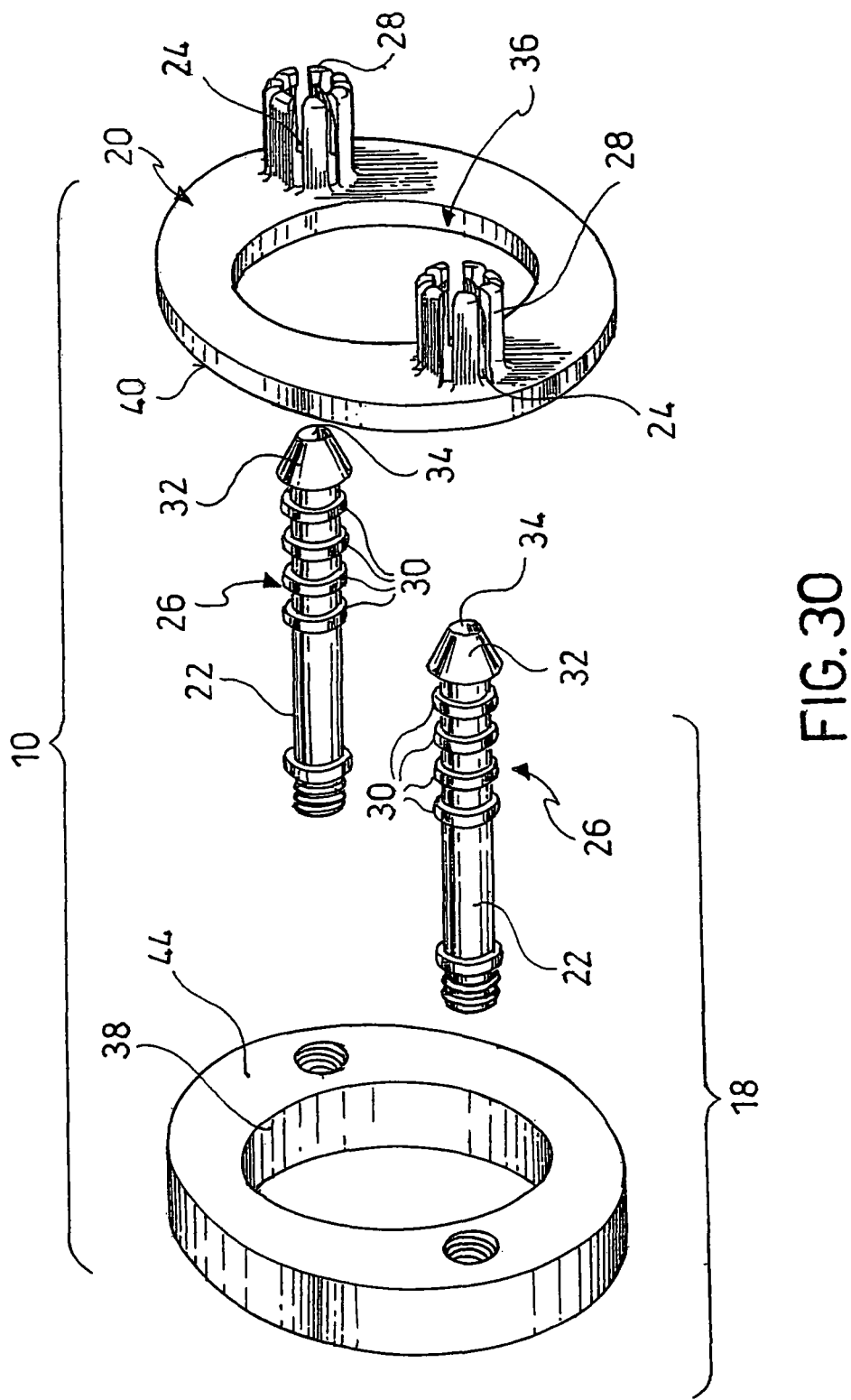
FIG. 30 illustrates a perspective and exploded view of an anastomotic device suitable for being used in some steps of the method.

With reference to FIG. 30, with 10 has been generally designated an anastomotic device according to a possible embodiment. FIGS. 18-28, 33 and 34 illustrate possible applications of the anastomotic device 10 or variant embodiments thereof.

In accordance with a first embodiment, the anastomotic device is suitable for approximating and keeping close to each other a first tissue portion 12 and a second tissue portion 14 that are intended to form an anastomosis 16. More particularly, the anastomotic device 10 is suitable for being used in a method, preferably endoluminally, for performing anastomoses in tracts of the digestive system. However, it can be optionally used in partially or wholly laparoscopic techniques or conventional surgical techniques.

FIG. 30 illustrates an exploded view of a preferred embodiment of the anastomotic device 10 in which an abutment portion has been designated with 18 and a locking portion has been designated with 20. Referring in particular to the application of the anastomotic device 10 in a method for carrying out a gastrojejunostomy (G-J), or similar methodologies, the abutment portion 18 can also be defined as the intestinal portion, while the locking portion 20 can also be defined as the gastric portion.

The abutment portion 18 is suitable for abutting against a surface of the first tissue portion 12, while the locking portion 20 is adapted to be arranged opposite the abutment portion 18 with respect to the first tissue portion 12 and to the second tissue portion 14.

In accordance with a generalized embodiment, the locking portion 20 and the abutment portion 18 are mutually connectable or couplable across the first and second tissue portions being drawn together, in order to keep them joined to each other. More particularly, the locking portion 20 and the abutment portion 18 are suitable for being mutually locked in at least two locking positions corresponding to different compression degrees of the first and second tissue portions.

In accordance with a preferred embodiment, the abutment portion 18 comprises at least one pin 22 suitable for passing through the first tissue portion 12 and the second tissue portion 14 and to enter a housing 24 of the locking portion 20 in order to fit thereto. Preferably the pin is adapted to snap fit and lock within the housing 24 of the locking portion 20. The snap fit is for example carried out by means of a pin 22 provided with at least one shaped portion 26 suitable for defining a snap connection with elastic tabs 28 that are associated to the respective housing 24 of the locking portion 20. Preferably, the elastic tabs 28 extend in the direction of the respective pin 22 away from the abutment portion 18 to extend the housing 24.

In the preferred embodiment as illustrated in FIG. 30, the shaped portion 26 is provided by means of a sequence of ring ribs 30. Furthermore, a free end of the pin 22 is shaped so as to promote the snap fitting, for example providing an outwardly tapering or frusto-conical end 32. Furthermore, the elastic tabs 28 are distributed along a peripheral edge of the respective housing 24 and extend in the direction and sense of insertion of the pin 22.

In accordance with a preferred embodiment, the pin 22 is movably mounted, preferably screwed, to the abutment portion 18.

In accordance with a preferred embodiment, the pin 22 defines internally a channel 34 that is opened on both sides and preferably adapted to receive a guide wire, as it will be described herein below. In accordance with this embodiment, also the respective housing 24 is adapted to receive the guide wire passing through the channel 34.

Referring to the annexed Figures, and in particular FIG. 30, the anastomotic device 10 comprises two pins 22, as described above, which extend from the abutment portion 18 and are adapted to be inserted in respective housings 24 of the locking portion. Preferably, the pins are located at opposite areas or sides of the abutment portion 18 and, similarly, the housings adapted to receive the pins are located at opposite areas or sides of the locking portion 20. When two pins are provided, as illustrated in the figures, it is particularly advantageous that each pin defines a channel 34 therein, which is adapted to receive a respective guide wire.

Optionally, two or more pins can be provided, as described above. If the number of pins corresponds to the number of the guide wires, each pin defines a channel 34 therein to receive a respective guide wire.

In accordance with a possible embodiment, the locking portion 20 presents an opening 36 to access the area intended for the formation of the anastomosis. In the case where two housings 24 are provided, these are located at opposite parts or sides of the opening 36. Preferably, the locking portion 20 is substantially ring-shaped.

Similarly, the abutment portion 18 has an opening 38 to access the area intended for the formation of the anastomosis and corresponding to the opening 36 of the locking portion. When two pins 22 are provided, these are preferably located at opposite parts or sides of the opening 38. Also the abutment portion 18 is, preferably, substantially ring-shaped.

Figure 33:
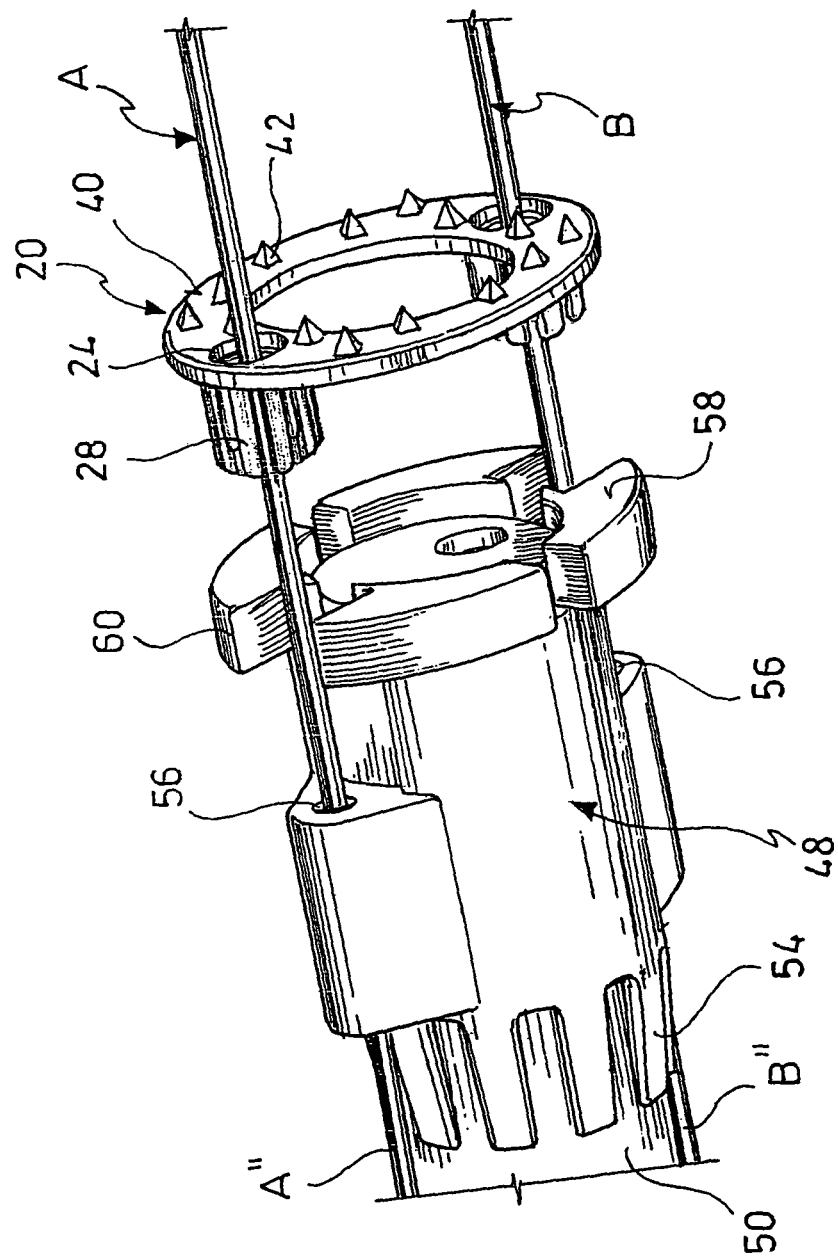
FIG. 33 illustrates a perspective view of the positioning device of FIG. 32 according to a different point of view and associated to a variant embodiment of a portion of the anastomotic device of FIG. 30.
Figure 34:
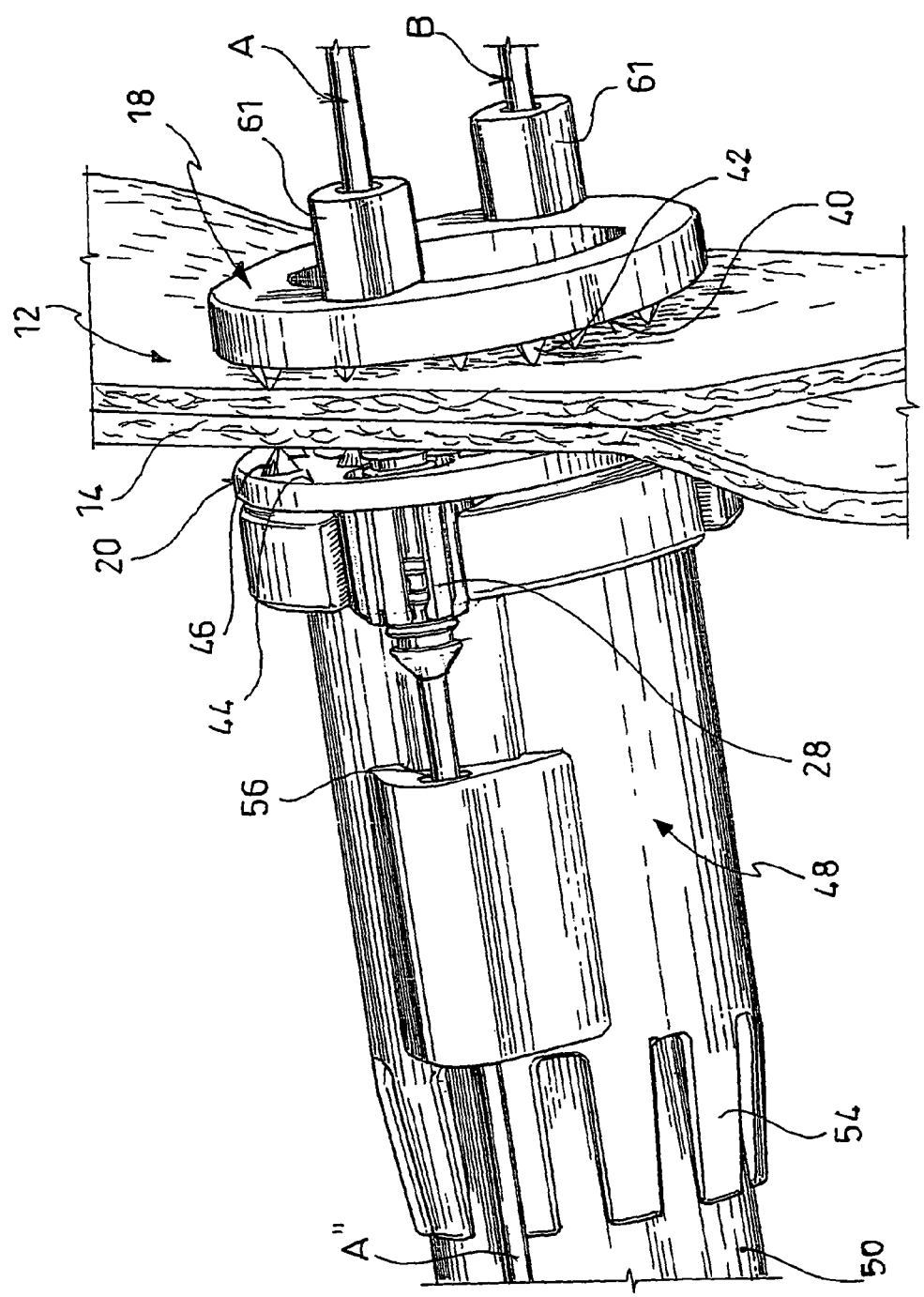
FIG. 34 illustrates a perspective view of a step of the method, carried out with a variant embodiment of the anastomotic device illustrated in FIG. 30.

A contact surface of the locking portion 20 suitable for the abutment against a surface of the second tissue portion 14 to approximate has been indicated with 40. This contact surface is a surface opposite to the extension of the elastic tabs 28, when provided. In accordance with a preferred embodiment, the contact surface 40 is rough or presents pointed members 42 (FIGS. 33 and 34). Optionally, annular grooves 43a can be provided (FIG. 37) or, the roughness can be imparted through a layer 43b made of reported material for example in granular form (FIG. 38).

In accordance with a possible embodiment, a contact surface of the abutment portion 18 suitable for the abutment against a surface of the first tissue portion 12 to be approximated has been indicated with 44. When at least one pin is provided, this contact surface is a surface located on the same side as the at least one pin 22. In accordance with a preferred embodiment, the contact surface 44 is rough or presents pointed members 46 (FIG. 34). Optionally, annular grooves 43a can be provided (FIG. 37) or, the roughness can be imparted through a layer 43b made of material reported for example in granular form (FIG. 38).

Generally speaking, and according to a first aspect of the present invention, the anastomotic device 10 is a device suitable for approximating and keeping close to each other a first tissue portion and a second tissue portion that are intended to form an anastomosis, which can be connected to a guide means, for example a guide wire or, preferably, at least two guide wires to reach the tissue portions, as it will be described below.

In particular, at least one of the abutment portion 18 and the locking portion 20 is suitable for being connected to a guide means comprising at least one guide wire to reach the first or second tissue portions.

Referring particularly to the annexed figures, the abutment portion 18 is suitable for being locked in a direction on the guide means, for example the guide wires A and B, which are preferably located on two opposite sides of the anastomotic device, through which it is dragged until reaching the first tissue portion 12. In other words, the abutment portion 18 is fastened to the guide wires such as to be dragged by the latter at the first tissue portion to draw the two tissue portions together, thus allowing the guide wires to be then taken off in the opposite direction.

Figure 17:
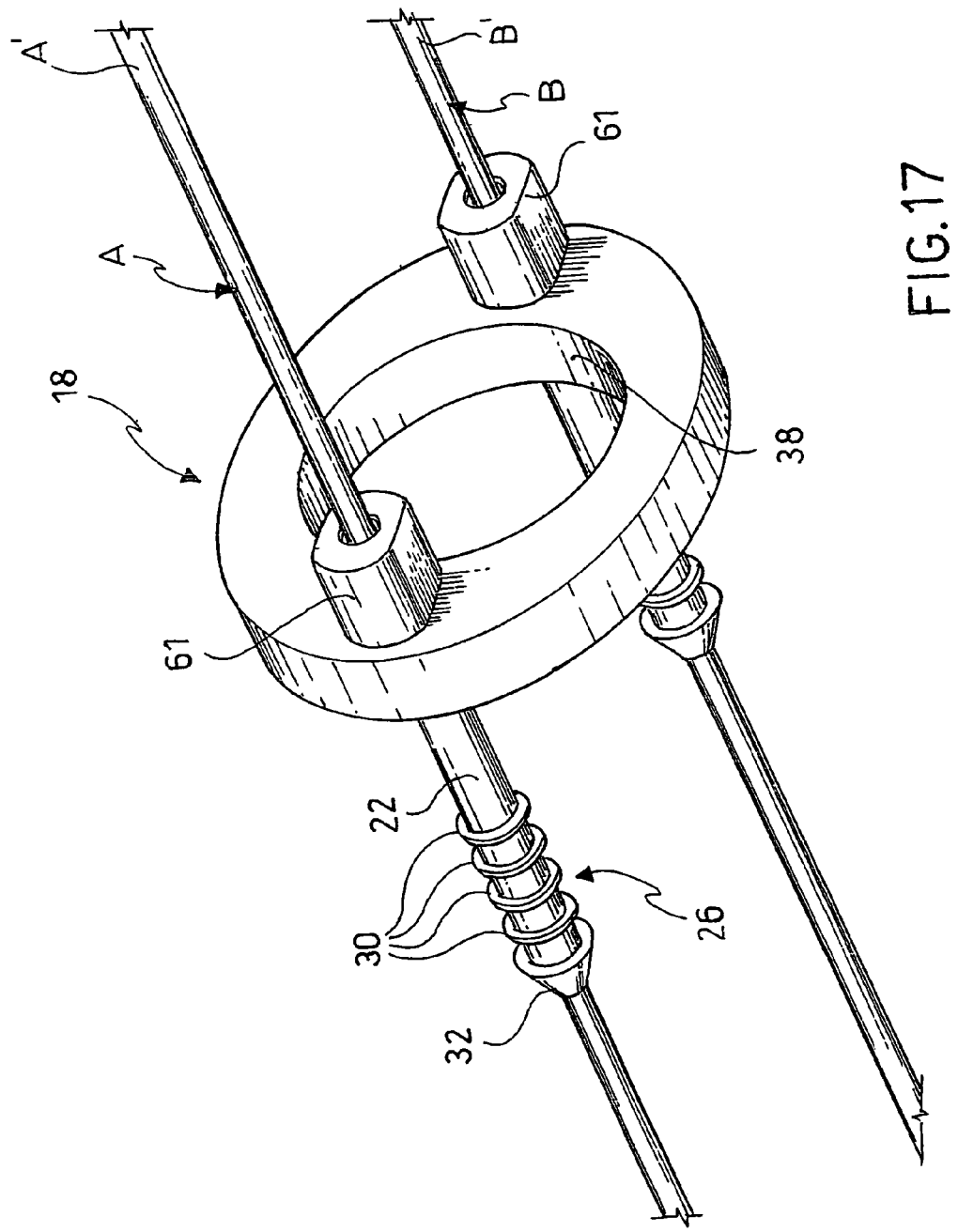
FIG. 17 illustrates a perspective view of a portion of an anastomotic device applied in a further step of the method.

In accordance with a possible embodiment, the abutment portion 18 is suitable for being locked on the guide wires A, B for example by means of locking members 61 made integral to a guide wire, respectively, and suitable for defining an obstacle for the sliding movement of the abutment portion 18 in a direction on the guide wires (FIG. 17).

In accordance with an advantageous embodiment, the abutment portion 18 comprises at least one channel suitable for receiving a guide wire. When two guide wires are provided, two channels located on opposite sides of the anastomotic device are advantageously provided. Furthermore, it is advantageously provided that the channels pass through the abutment portion 18.

In accordance with a possible embodiment, the guide means pass through the abutment portion 18 and the locking portion 20 at connecting members between the two portions. According to a preferred embodiment described above, in which the anastomotic device 10 comprises at least one pin in order to be connected to the locking portion 20, it is advantageously provided that this pin 22 defines a channel 34 suitable for receiving a guide wire. Particularly, according to a further preferred embodiment in which the anastomotic device 10 comprises at least two pins 22 to be connected to the locking portion, is advantageously provided that the two pins 22 define a channel 34 adapted to receive a guide wire, respectively.

In accordance with a preferred embodiment, the locking portion 20 is adapted to slide along the guide means and presents an interacting portion with said positioning device 48 which biases the latter along said guide means.

It should be understood that variations and/or additions to what has been described and illustrated above may be provided.

For example, the pins 22 can be made as one piece with the abutment portion 18. Or, the pins can extend from the locking portion 20 and be inserted in housings of the abutment portion 18.

The anastomotic device 10 can be made of any type of material suitable for surgical applications. In addition to what has been stated above, in particular in the case of an anastomotic device 10 suitable both for approximating and keeping the tissue portions close to each other, both the abutment portion and the locking portion can be made in not-bioabsorbable material, for example in plastic or metallic material. In this case, the anastomotic device 10 spontaneously detaches and moves away when the tissue to which it is attached necrotizes. According to a different embodiment, the anastomotic device can be made such as to stay in a steady position.

Alternatively, the choice of the material can be directed towards a bioabsorbable or biofragmentable material, thus providing that the anastomotic device is completely absorbed after a preset period of time.

Finally, the anastomotic device 10 can be partially made of bio-absorbable or biofragmentable material. In particular, it is advantageous to provide that the connecting members between the abutment portion and the locking portion are made of bioabsorbable or biofragmentable material, in order to allow the anastomotic device to disengage from the site to which it has been applied after a preset period of time and to spontaneously move away. In the case illustrated in the annexed drawings, it can be advantageously provided that the pins 22 and/or the housings 24 and/or the elastic tabs 28 are made in bioabsorbable or biofragmentable material.

An anastomotic device 10 suitable for approximating and keeping close to each other a first tissue portion 12 and a second tissue portion 14 that are intended to form an anastomosis 16 can generally be made in such a way that the abutment portion and the locking portion are mutually connectable across the first and second tissue portions drawn together in order to keep them joined to each other. In particular, also an individual pin 22 can be provided and optionally different from the housing channel of the guide wire. Furthermore, it can be provided that this anastomotic device can be inserted and locked even on an individual guide wire or on more than two guide wires.

It is described below the mode of use of an anastomotic device according to the preferred embodiments illustrated and according to the two above described aspects of the invention. The application example relates to a method for performing anastomoses in tracts of the digestive tube, and in particular to a method for endoluminally performing a gastrojejunostomy, for example as illustrated in FIGS. 18-28. Other applications are possible, such as a jejuno-jejunostomy, generally an entero-enteroanastomosis or other kinds of anastomosis.

Figure 18:
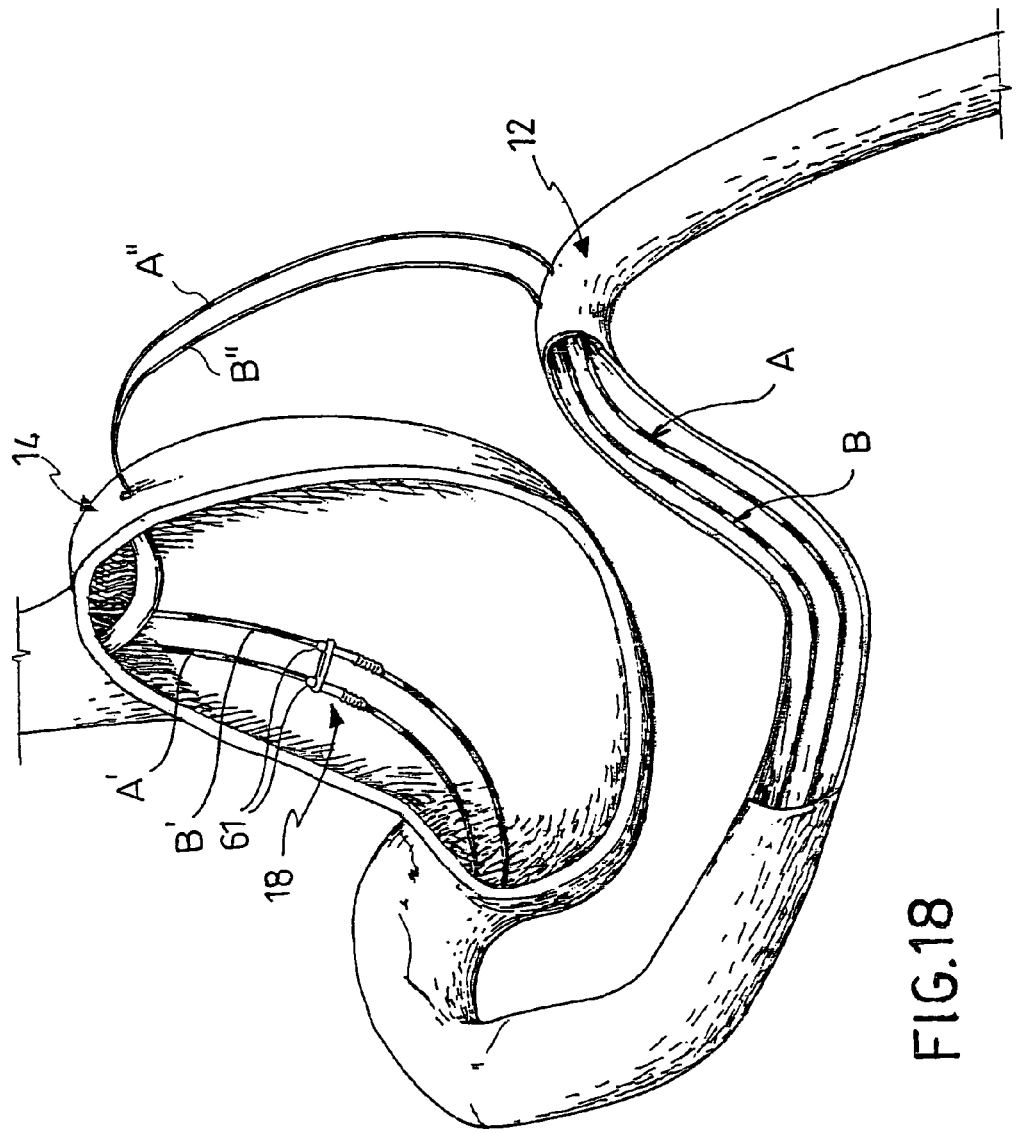
FIG. 18 illustrates a further step of the method carried out on the portion of FIG. 16.
Figure 19:
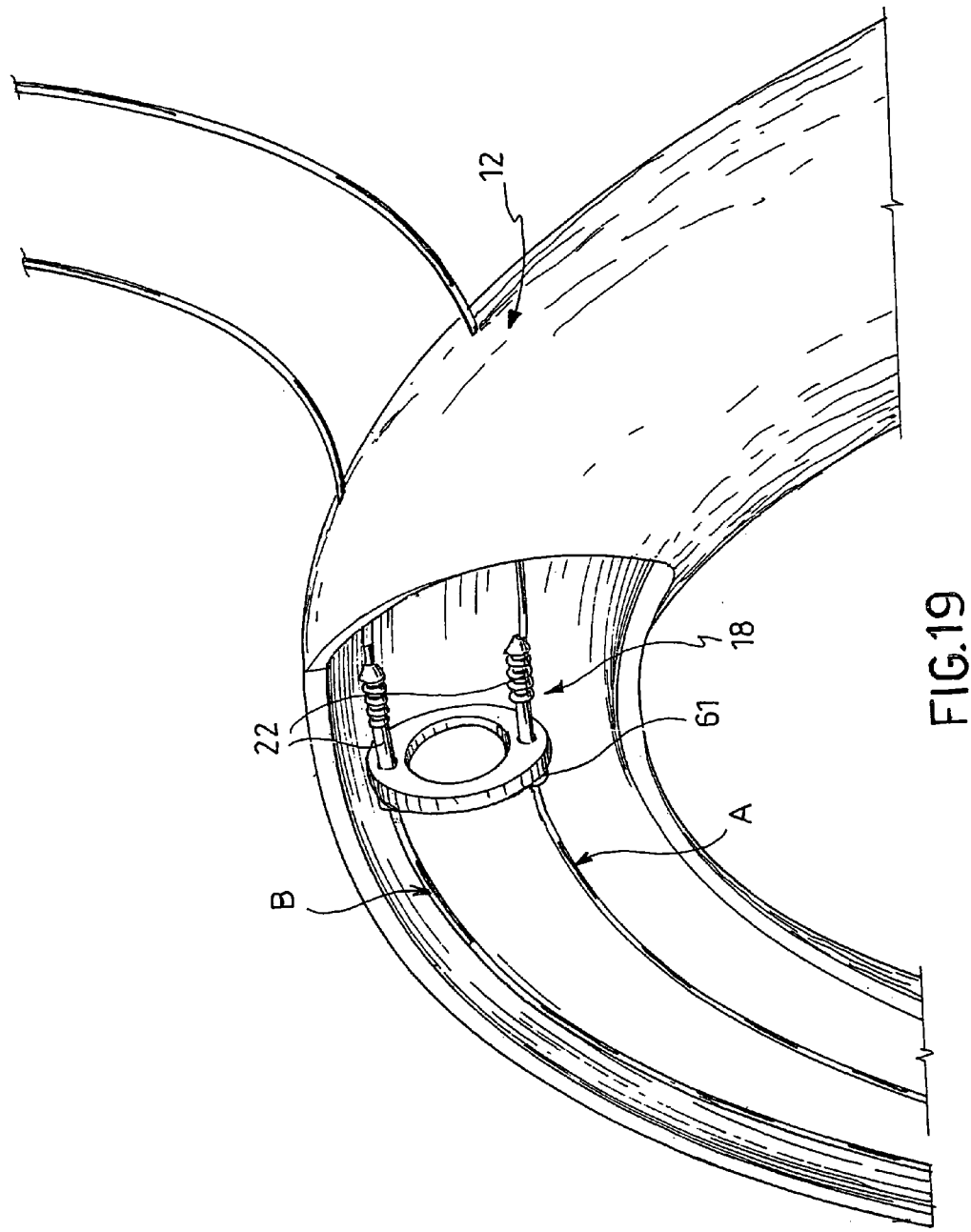
FIGS. 19 and 20 illustrate perspective and enlarged views of a detail from FIG. 18 corresponding to further steps of the method, respectively.

In FIG. 18 a portion of the digestive system comprising stomach and an intestine tract, corresponding to a jejune tract is illustrated. A guide means for example comprising two guide wires has been located starting from a natural orifice, such as the oesophagus, and forms an open ring or loop which passes through the first tissue portion 12 and the second tissue portion 14. The two guide wires A and B extend between proximal end portions A' and B' and distal end portions A" and B". The abutment portion 18 of the anastomotic device 10 is inserted on proximal end portions of the guide wires and locked, for example by means of locking members 61 that are firmly connected or made integral to a guide wire, respectively, and suitable for defining an obstacle to the sliding of the abutment portion 18 on said guide wires (FIG. 17). Alternatively, other locking means can be provided, for example integrated in the anastomotic device structure. Optionally, the abutment portion 18 is pre-connected or integral to the guide wires in such a way that when the distal ends of the guide wires are dragged, the abutment portion is dragged and drawn against the tissue portions to be connected.

Figure 20:
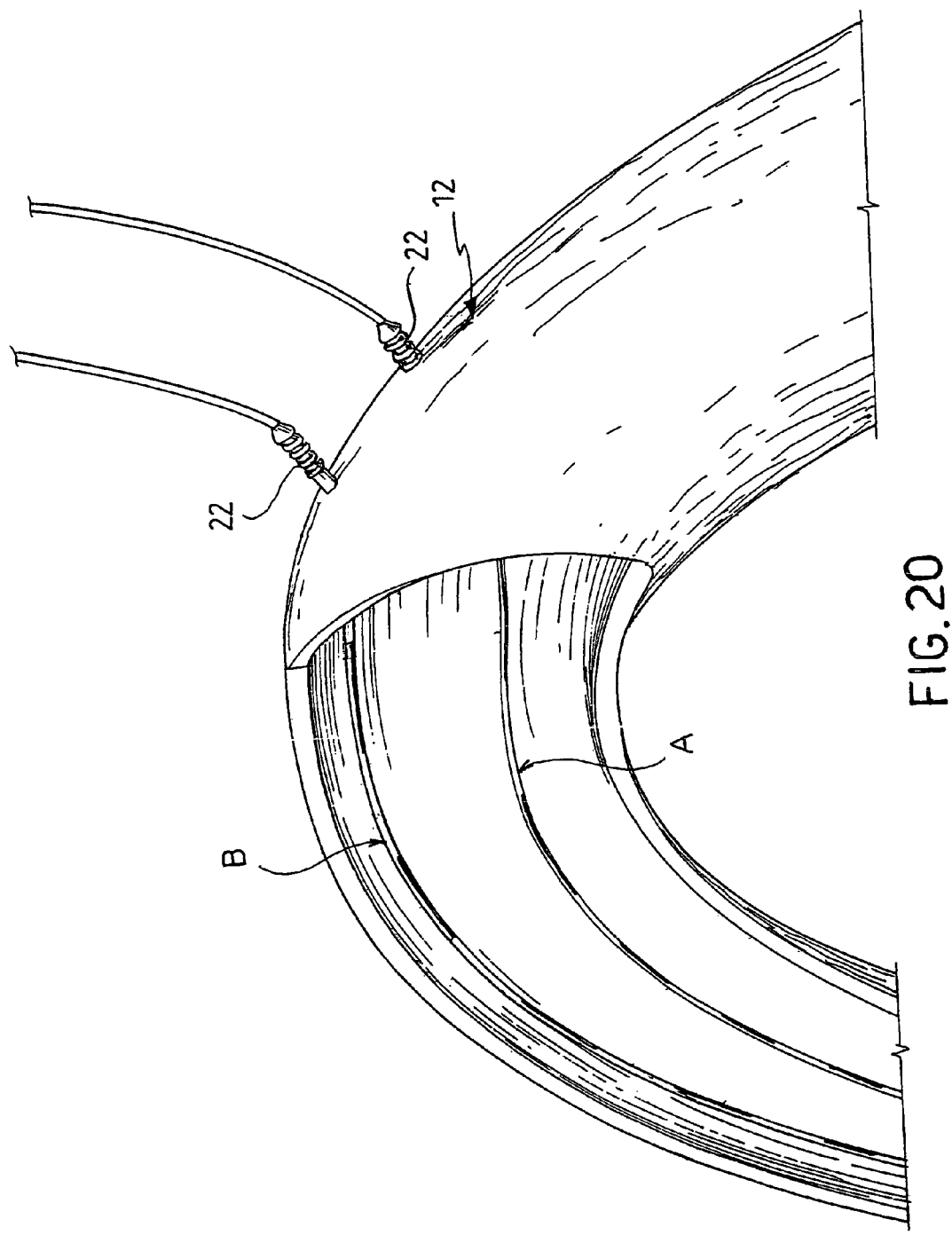

The abutment portion 18 is subsequently drawn together to the first tissue portion 12 by pulling distal end portions of the guide wires (FIG. 19) until the pins 22 are inserted into and pass through the first tissue portion 12 (FIG. 20).

Figure 21:
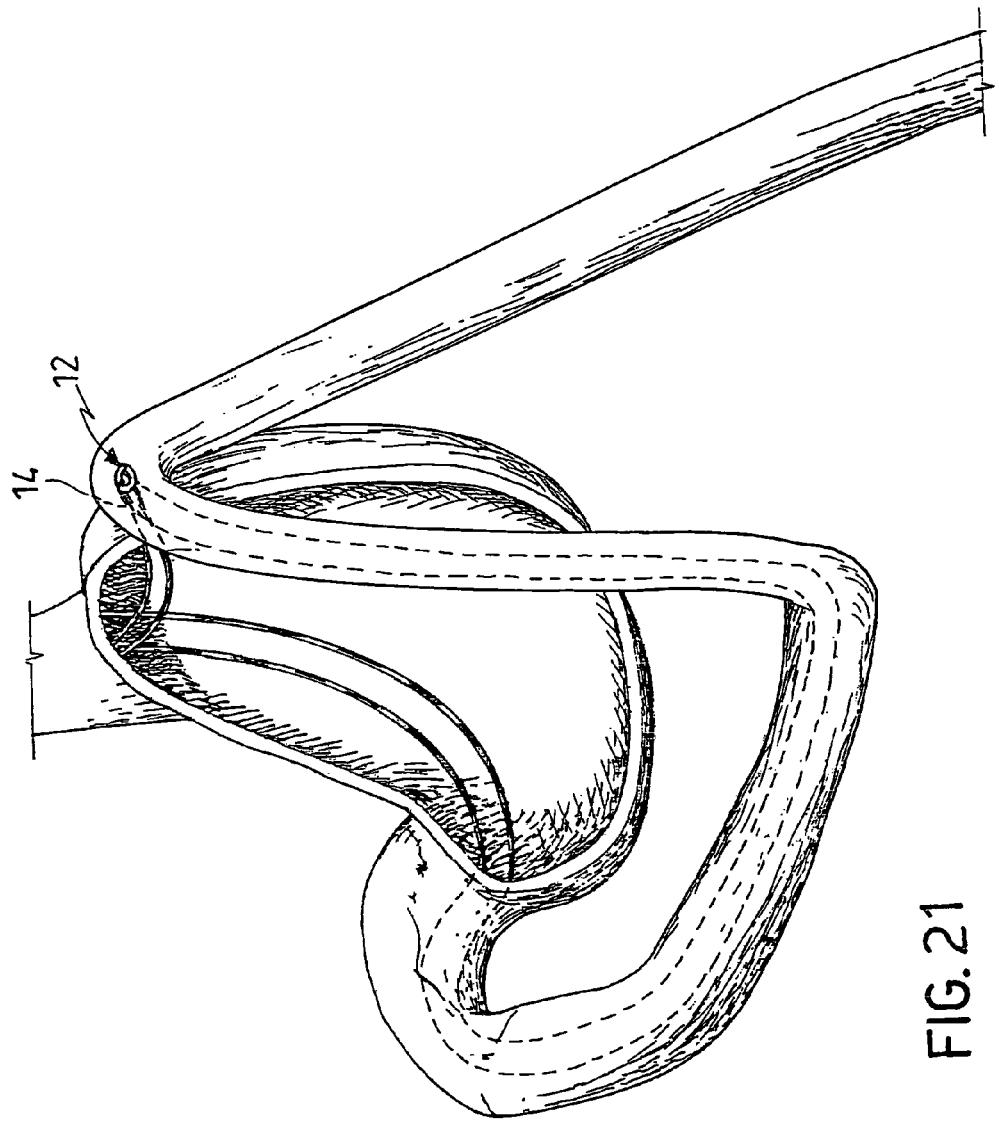
FIG. 21 illustrates a further step of the method carried out on the portion of FIG. 15.

The contact surface 44 abuts internally against the first tissue portion 12, thereby a further traction performed on the distal end portions of the guide wires causes the first tissue portion 12, dragged by the abutment portion 18, to be drawn together with the second tissue portion 14 (FIG. 21). In other words, FIGS. 18-21 illustrate an application of an anastomotic device 10, i.e. an anastomotic device suitable for approximating a first tissue portion and a second tissue portion that are intended to form an anastomosis.

Figure 22:
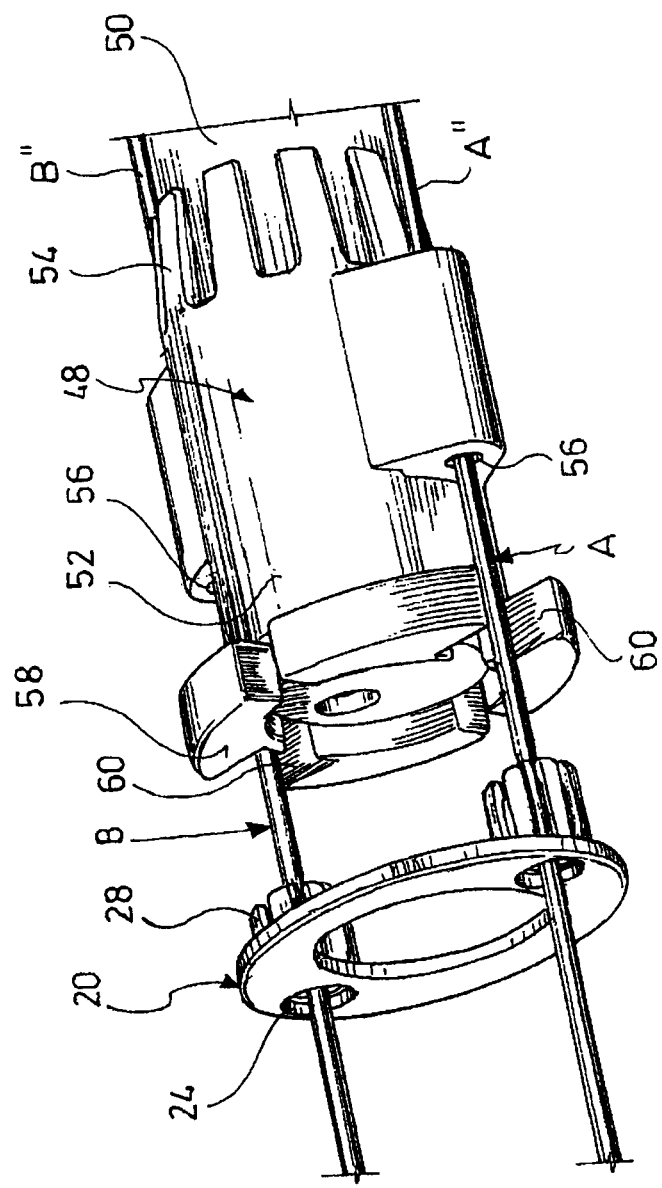
FIG. 22 illustrates a perspective view of a portion of an anastomotic device and a positioning device according to the present invention being applied in a further step of the method.

Due to its shape, the anastomotic device 10 can be used not only to draw together but also to keep close the two tissue portions to each other. This application is further illustrated in FIGS. 22-28, in which the application of the locking portion 20 is shown, preferably biased in position along the guide wires by the positioning device 48. The locking portion 20 is inserted on the distal end portions A" and B" of the guide wires through the housings 24. The head 52 is also subsequently inserted on the distal end portions of the guide wires through the channels 56. Finally, the head 52 is fitted on the distal end of the elongated structure 50, or gastroscope (FIG. 22). The positioning device 48 interacts with the locking portion 20 via the thrust surface 58 and the elastic tabs 28 are inserted in the respective openings 60.

Figure 23:
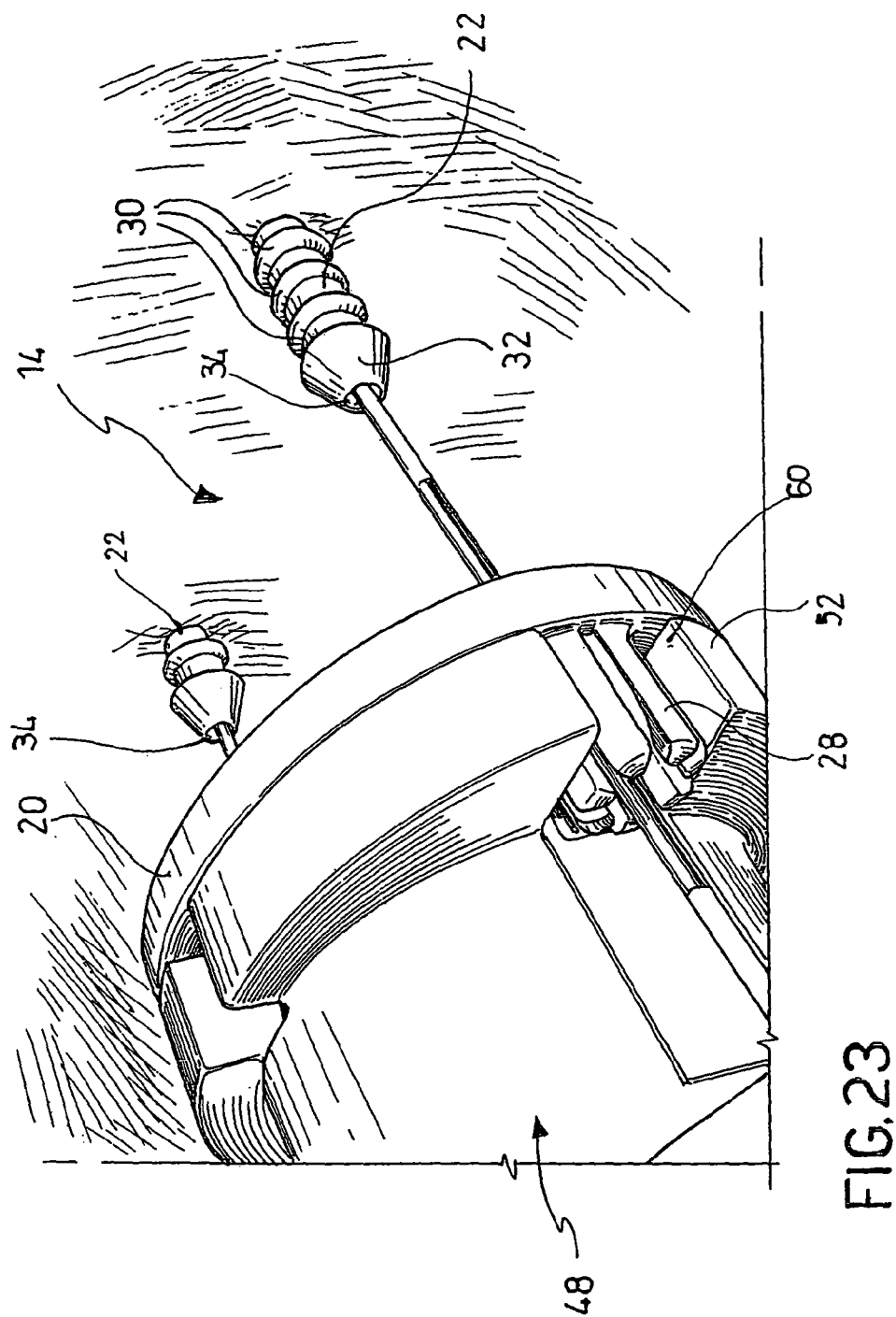
FIG. 23 illustrates a perspective view and from the interior of the stomach of a further step of the method.
Figure 24:
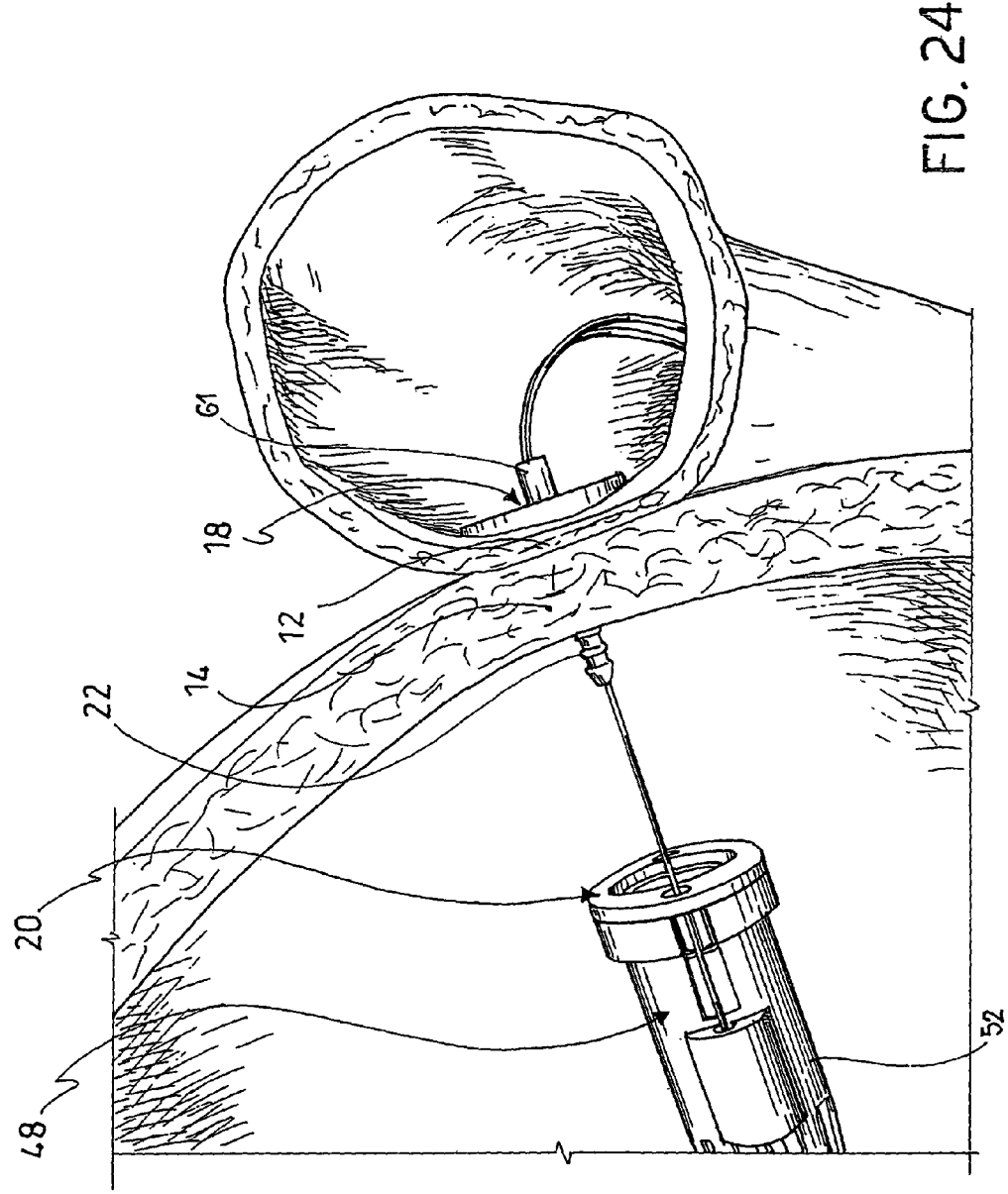
FIG. 24 illustrates the view in FIG. 23 from a different point of view.

The head 52 biases the locking portion 20 in position by sliding on the guide wires until approaching to the second tissue portion 14, oppositely of the abutment portion 18, i.e. on the stomach side (FIGS. 23 and 24).

Figure 25:
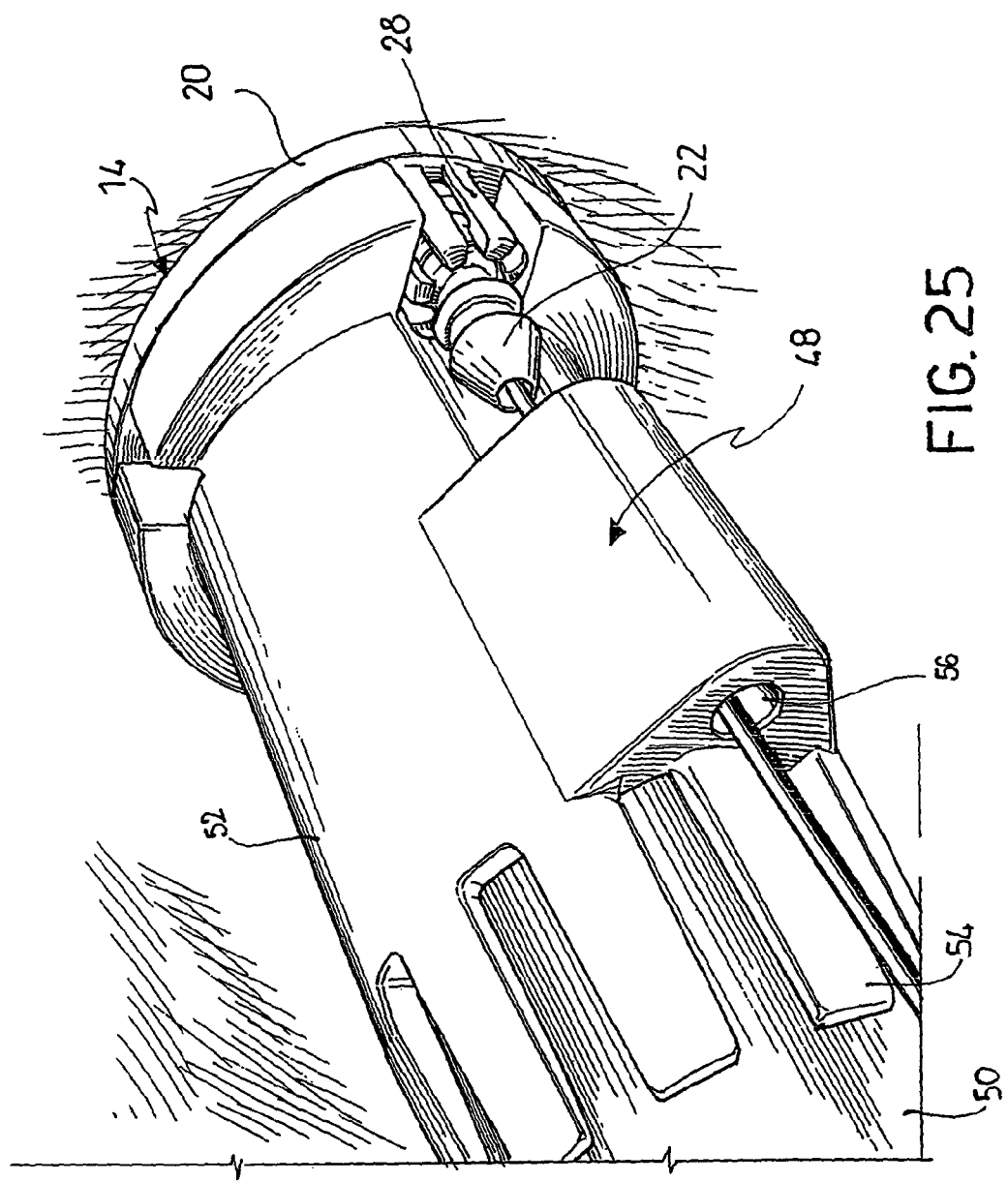
FIG. 25 illustrates a perspective view and from the interior of the stomach of a further step of the method.
Figure 26:
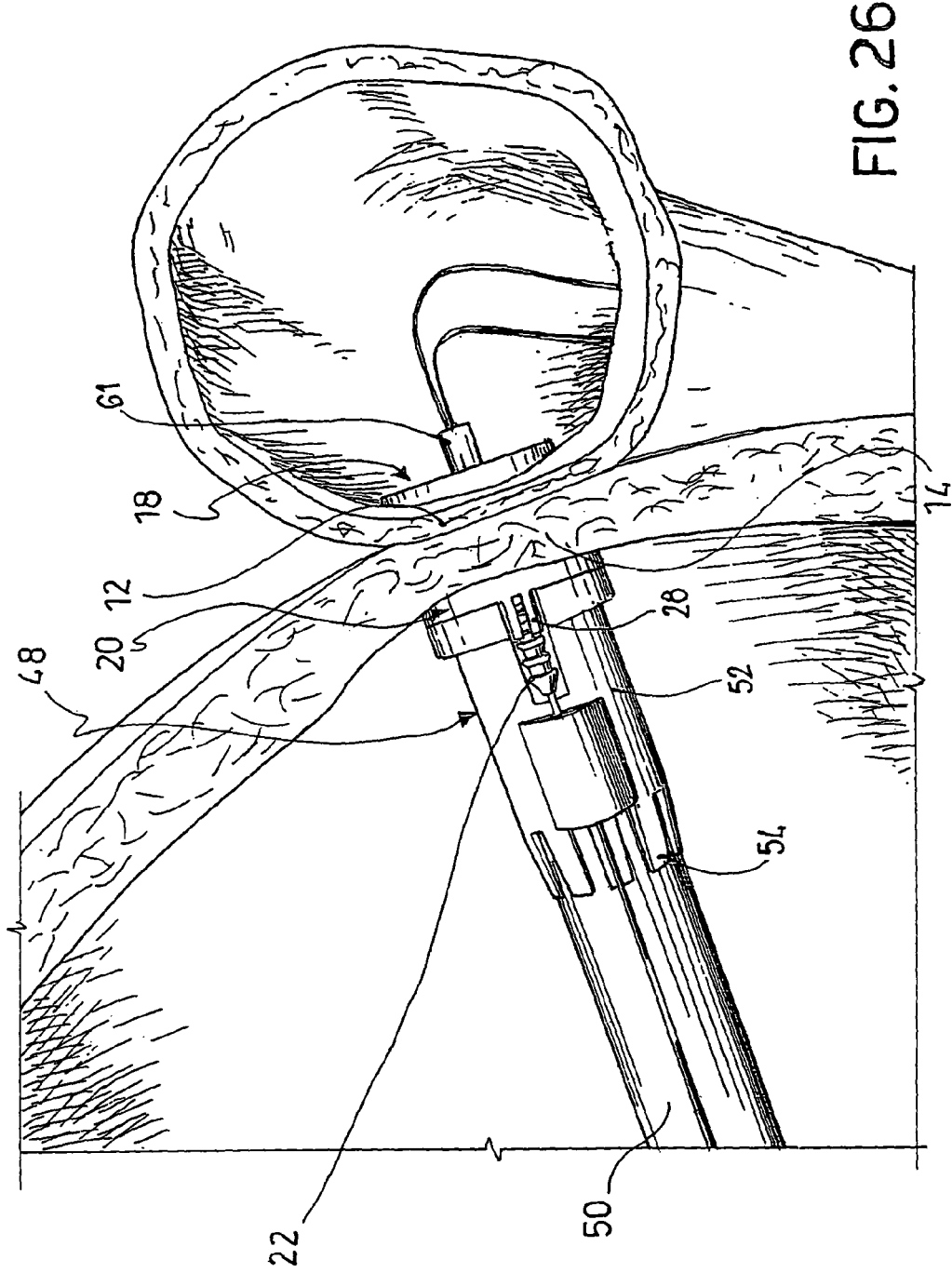
FIG. 26 illustrates the view in FIG. 25 from a different point of view.
Figure 27:
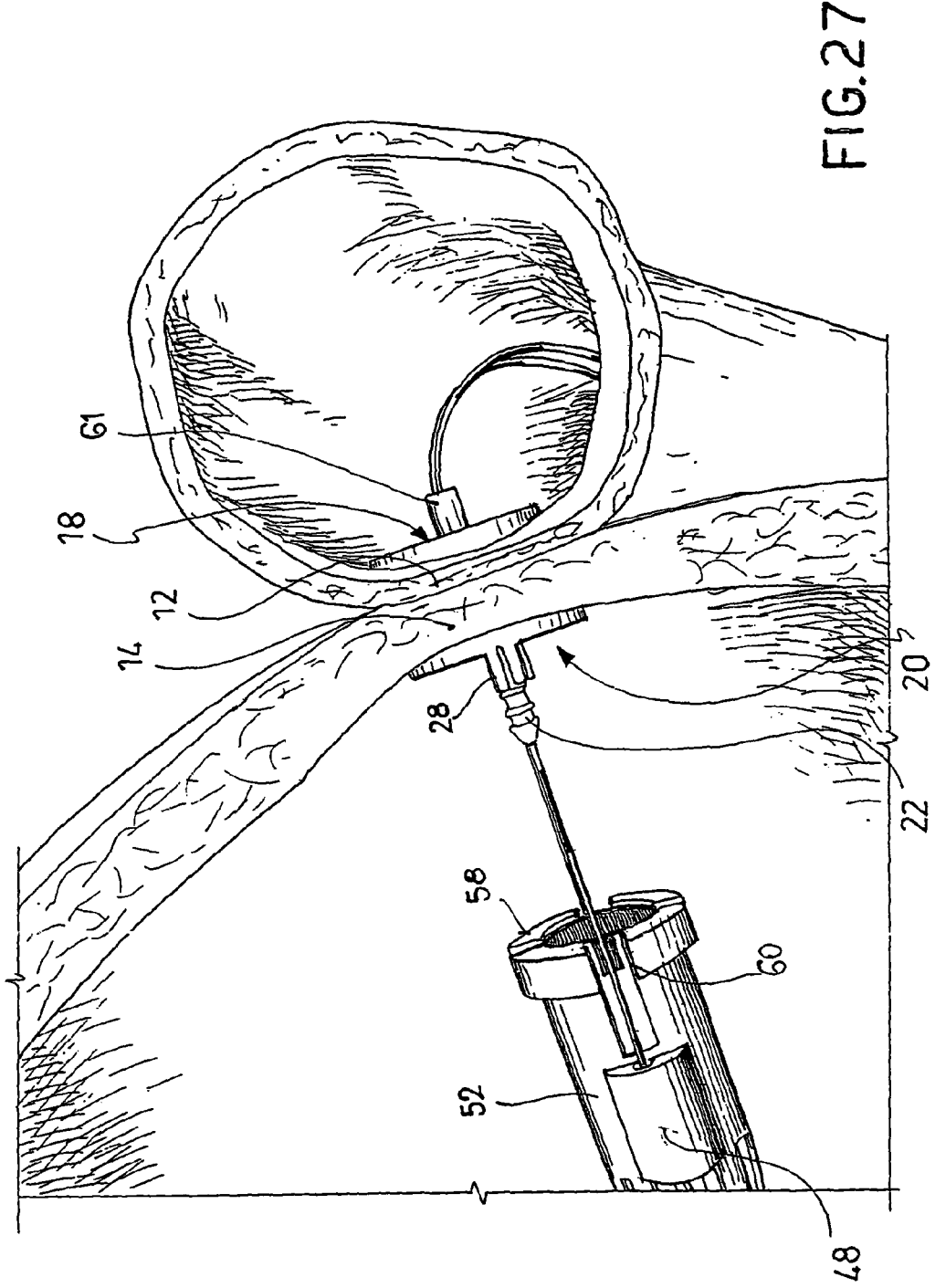
FIG. 27 illustrates a perspective view and from the interior of the stomach of a further step of the method.
Figure 28:
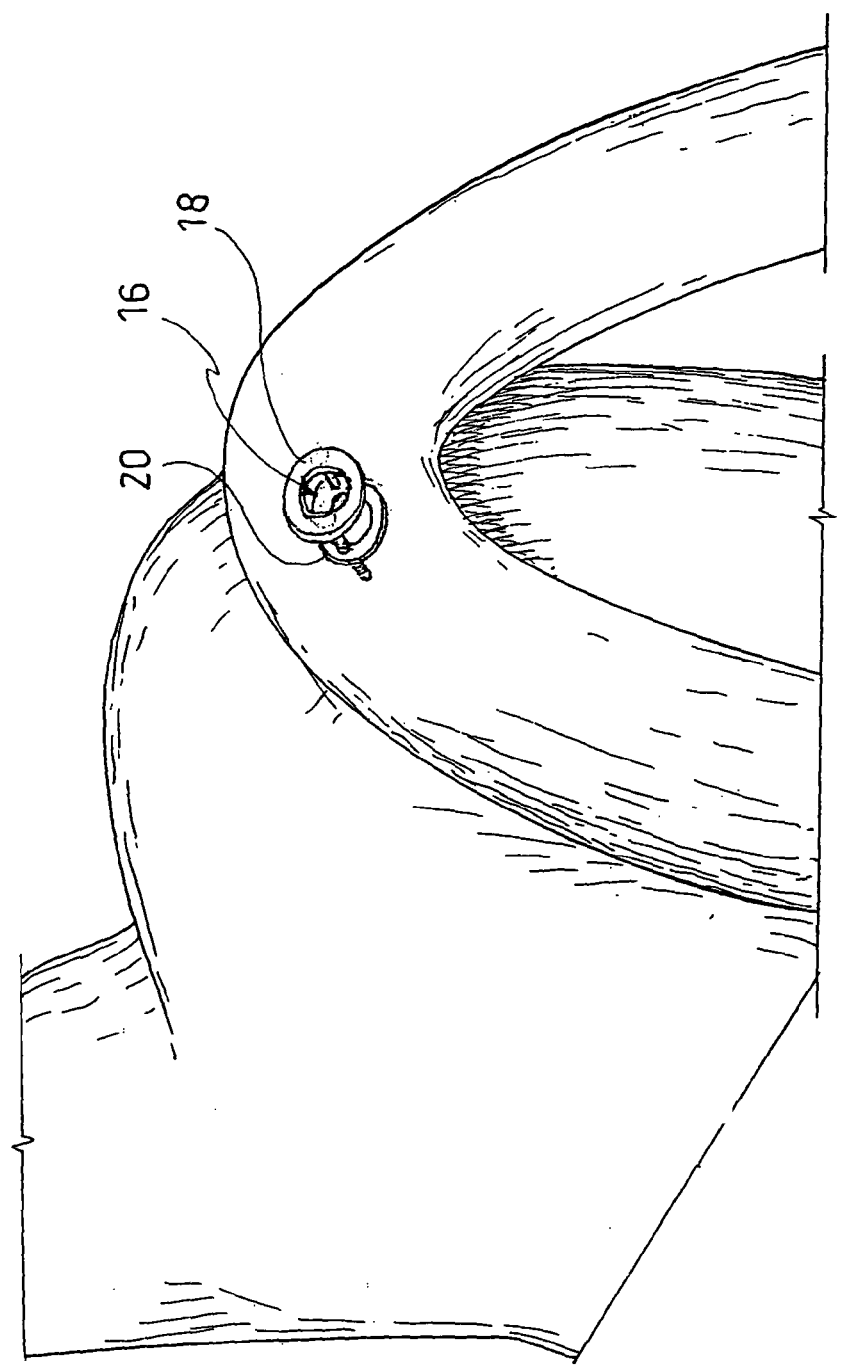
FIG. 28 illustrates a perspective, enlarged and partially phantom view of a detail of the portion of FIG. 1 at the end of a third sequence of steps of the method.
Figure 29:
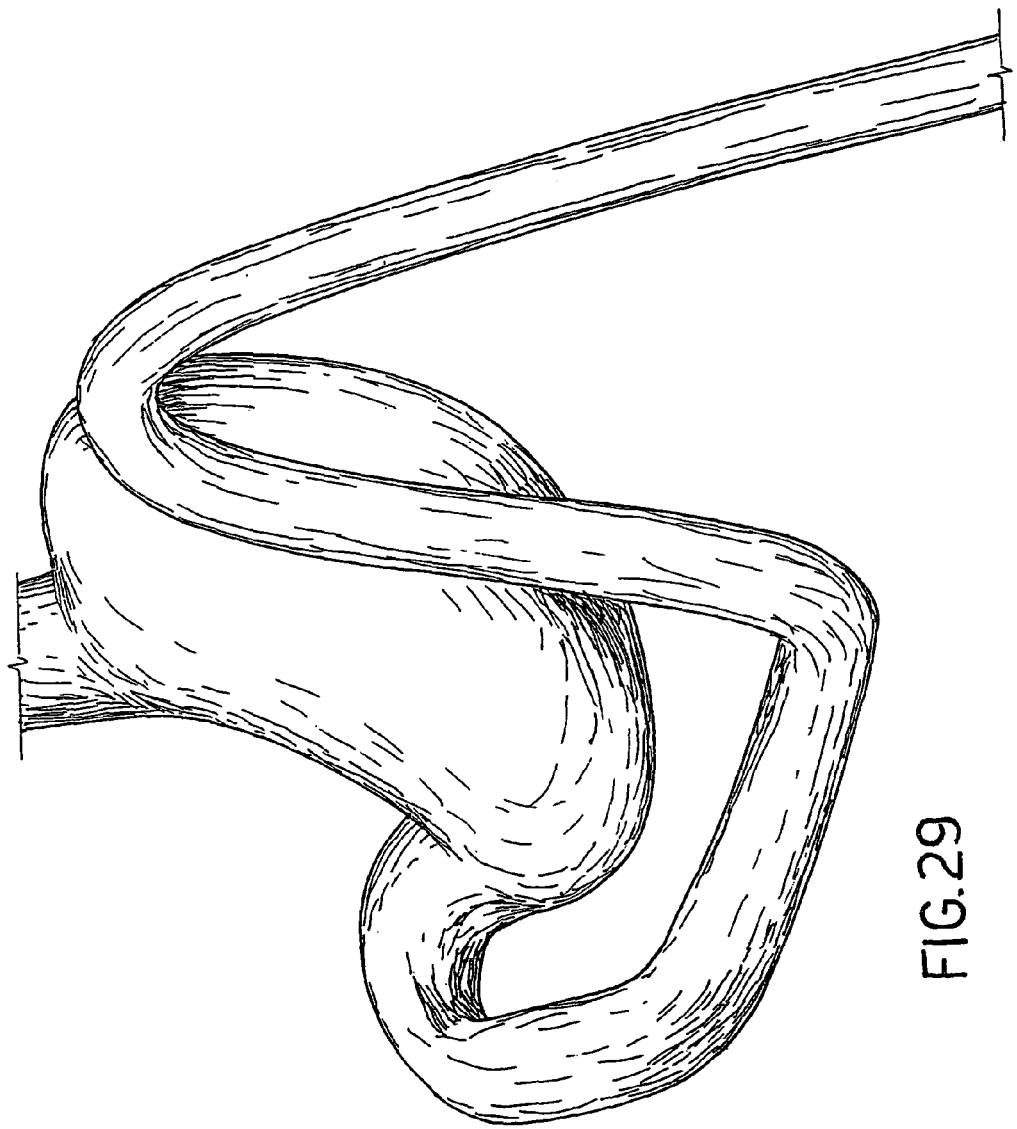
FIG. 29 illustrates a perspective view of the portion of FIG. 1 at the end of the third sequence of steps of the method.

By keeping to bias the elongated structure 50 along the guide wires, the pins 22 are inserted in the housings 24 of the locking portion and the frusto-conical end 32 enlarges the elastic tabs 28, which abut between a ring rib 30 and the next one, thus providing a snap fit (FIGS. 25 and 26). The bias exerted on the locking portion 20 via the head 52 and the elongated structure 50 allows selecting one of the possible mutual positions of the abutment portion 18 and the locking portion 20. In other terms, the provision of ring ribs 30 allows to define at least two relative positions between the abutment portion 28 and the locking portion 20, in order to set an optimum compression degree of the tissues, which can be assessed as a function of their more or less ischemic coloration.

By withdrawing the positioning device 48, the locking portion 20 remains attached to the abutment portion 18 allowing to keep the two tissue portions (FIGS. 27 and 28) joined to each other. Subsequently, the anastomosis can be completed as will be described below.

The use of an anastomotic device as described above allows to provide an efficient and user-friendly tool, and moreover a tool suitable for performing endoluminally anastomoses of tracts of the digestive tube, even if its use is possible also in other techniques, for example partially or wholly laparoscopic techniques or conventional surgical techniques.

A first object of the device is to provide an abutment portion which allows two tissue portions to be approximated, which are to be connected by anastomosis. As this device can be connected, or even locked, on at least two guide wires, it allows to control and direct the anastomotic device throughout the path within the digestive system, both to draw together and connect the two tissue portions.

By providing an annular conformation which connects on two opposite sides two guide wires, it is possible to perform the anastomosis within the anastomotic device used to draw the tissues together. A possible completion step of the anastomosis will be described below.

The provision of two portions suitable for being connected or coupled to each other allows the same device to be used both to draw and keep the two tissue portions drawn together. The locking is easy and effective, because it is done in a snap manner, furthermore with the possibility to define different compression degrees of the tissues.

The latter aspect may be independent of the presence of one or more guide wires, even if the combination of the two aspects allows to accurately control and direct also the locking step, in particular in the case where the guide wires pass through the pins and the connecting housings between the two portions. As a consequence, it a very compact anastomotic device is further achieved.

A method is described below for performing anastomosis in tracts of the digestive tube in which a positioning device is used such as described above.

This method generally comprises the steps of:

introducing, through a natural orifice or other luminal structures, at least one guide wire (A, B) extending between proximal end portions (A', B') and distal end portions (A", B") and passing through a first tissue portion (12) and a second tissue portion (14) in which the anastomosis has to be performed, locking an abutment portion 18 of an anastomotic device 10 by inserting the latter on said proximal end portion of said at least one guide wire and drag it by means of said at least one guide wire until when the first tissue portion and the second tissue portion are drawn together, inserting a locking portion 20 of said anastomotic device 10 on the distal end portion A", B" of said at least one guide wire on the opposite side of the abutment portion 18 relative to the first and second tissue portions, pushing said locking portion 20 along said at least one guide wire by means of a positioning device as described above, until it is coupled with connecting elements of the abutment portion 18, which pass through the first and second tissue portions, completing the anastomosis at openings 36, 38 of the abutment portion 18 and locking portion 20.

Preferably, the positioning device is suitable for sliding along said at least one guide wire. Most preferably, the guide means comprises at least two guide wires A, B placed side by side, and the positioning device is suitable for sliding along said at least two guide wires.

Advantageously, the guide wires are arranged to form a loop with end portions at natural orifices or other orifices. The loop passes through the first tissue portion 12 and the second tissue portion 14 to be connected, and the anastomotic device 10 is inserted on the ring-shaped guide wires A and B.

Referring to annexed figures, a method for performing a gastro-jejunoanastomosis has been illustrated, in which a positioning device and an anastomotic device 10 are used. It should be understood that further and different uses are possible, for example in a method for performing generally entero-enteroanastomosis or, more particularly, jejuno-jejunoanastomosia or ileo-jejunanastomosis A first step of the aforesaid method provides for the introduction, through a natural orifice or other luminal structures, of at least two guide wires A and B placed beside, for example substantially parallel, to each other. The guide wires extend between proximal end portions A' and B' and distal end portions A" and B" and pass through a first tissue portion 12 and a second tissue portion 14 where the anastomosis is to be performed. The guide wires can be introduced such as to remain at least partially placed side by side at a determined distance from each other or placed side by side and drawn together. In accordance with what has been illustrated above, the guide wires are spaced apart from each other both during the introduction step and during the step of passing through the first tissue portion to be connected by means of anastomosis. According to an alternative embodiment, the guide wires are drawn together and placed side by side also during the introduction and the passing-through step of the first tissue portion. In the latter case, they can also be connected at the distal end to be subsequently separated when the insertion has been completed.

Then, the aforesaid method provides the insertion of an anastomotic device along the two guide wires and dragging it to the anastomotic site, by drawing the first tissue portion and the second tissue portion together and performing an anastomosis. Optionally, the abutment portion 18 is pre-connected to the guide wires in such a way that when the distal ends of the guide wires are dragged, the abutment portion is dragged and drawn to the tissue portions to be connected.

In particular, the two guide wires are located so as to form a loop with the end portions at natural orifices, or other orifices, while the loop passes through the first tissue portion 12 and the second tissue portion 14 to be connected. The anastomotic device is inserted along the two loop-shaped wires to perform the anastomosis, preferably endoluminally.

The distal ends of the two guide wires are first inserted to the first tissue portion 12 and introduced therethrough until they pass therethrough and project oppositely.

Preferably, the two guide wires are inserted by means of an insertion device 62 at least until they reach and pass through the first tissue portion 12.

Figure 31:
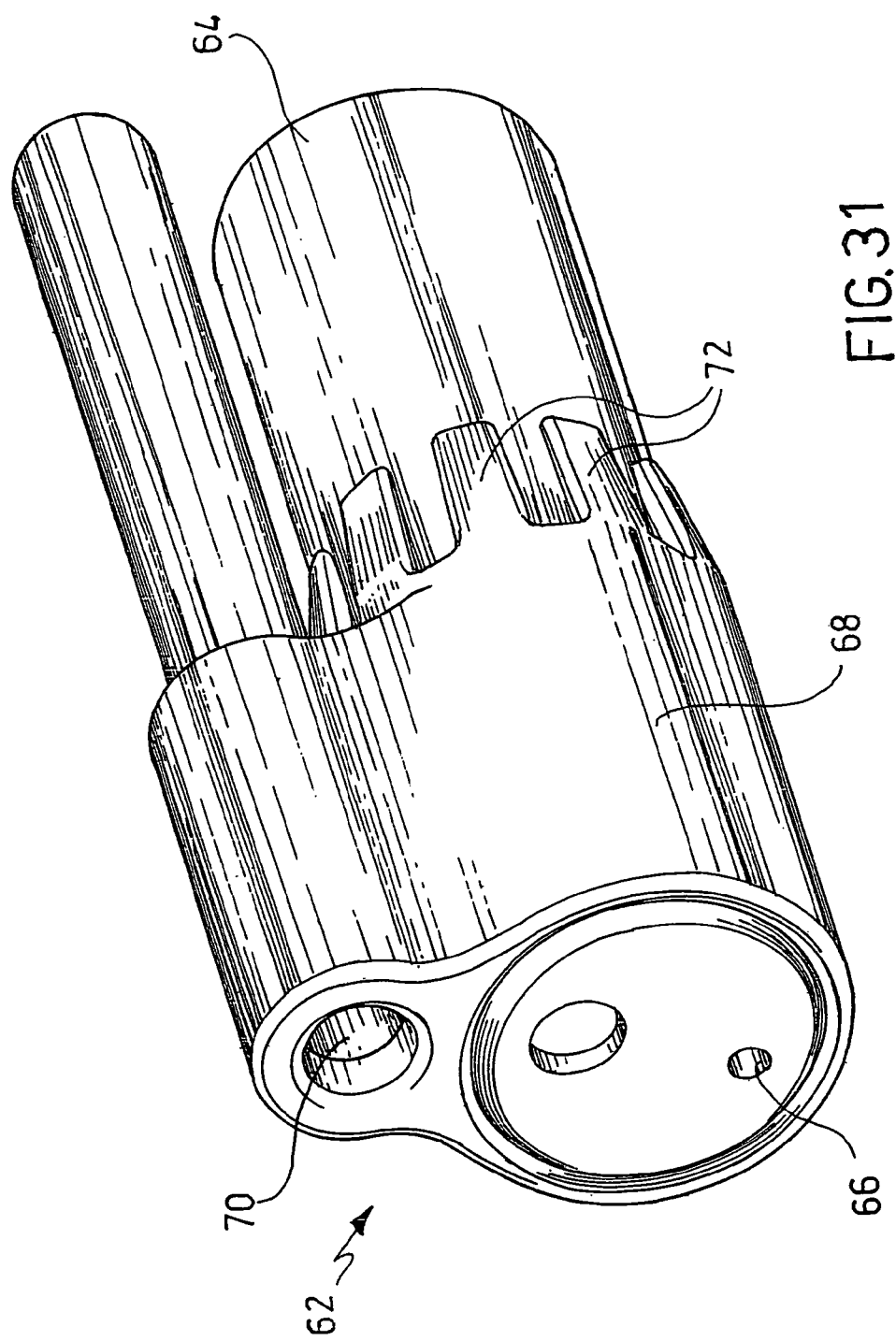
FIG. 31 illustrates a perspective and enlarged view of a detail of an insertion device suitable for being used in some steps of the method.
Figure 32:
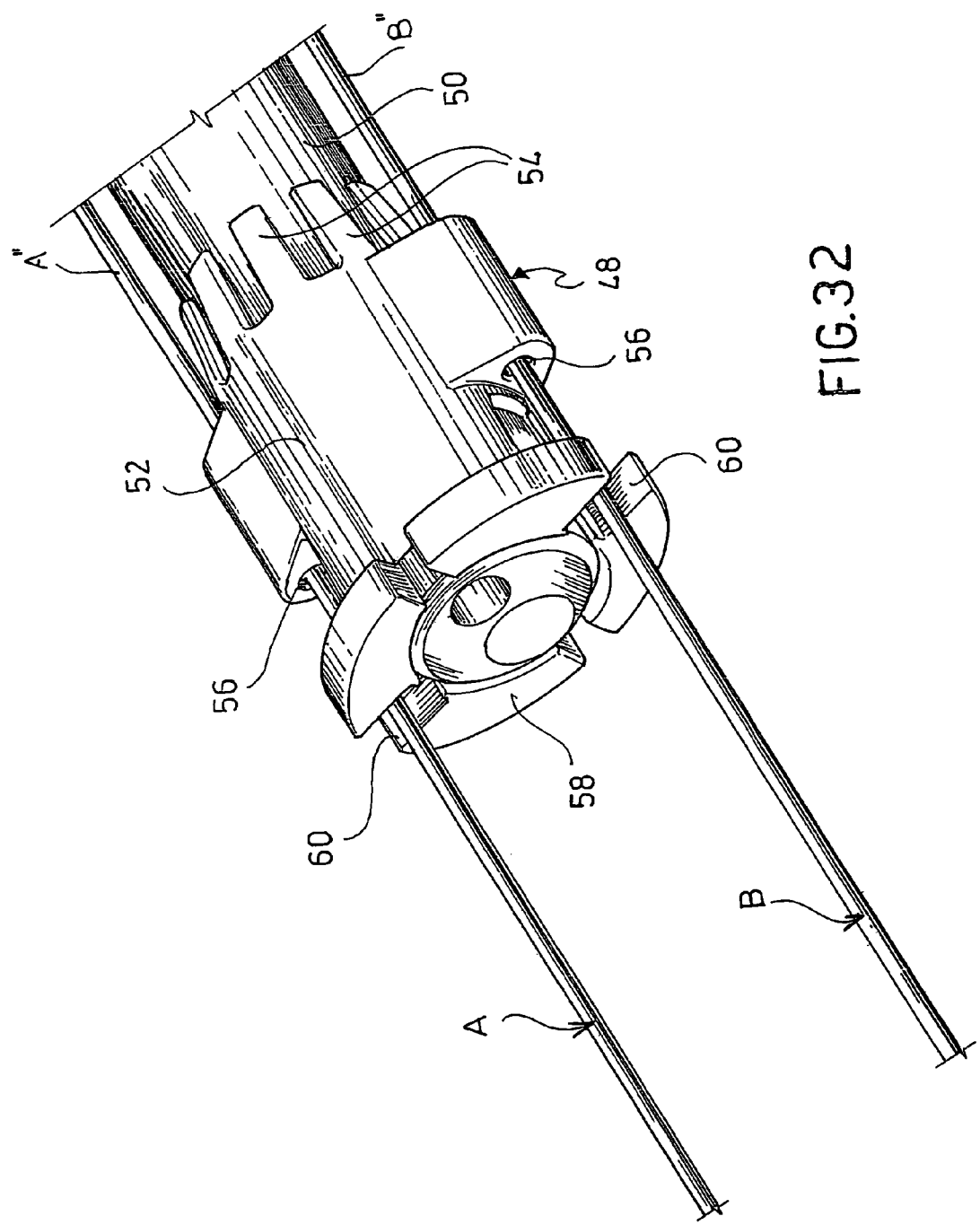
FIG. 32 illustrates a perspective view of a positioning device according to the present invention suitable for being used in some steps of the method.

Referring to the FIG. 31, the insertion device 62 comprises an elongated structure that is preferably provided by means of a visualization device, for example, a gastroscope 64, provided with a first operative channel 66 suitable for receiving and inserting one of the guide wires. Advantageously, a connecting head 68 suitable for being mounted to a distal end of the elongated structure (visualization device 64) can be further provided. The connecting head 68 is integral with at least one second operative channel 70 suitable for receiving and inserting another guide wire of said guide wires. The operative channel 70 extends substantially throughout the length of the elongated structure to keep the two guide wires distinct during the insertion. Advantageously, the second operative channel 70 is located externally to the elongated structure, made integral with the latter by means of the connecting head 68.

In particular, the first and second operative channels are suitable for displacing a guide wire, respectively, in a method for performing anastomoses in tracts of the digestive tube.

Advantageously, the operative channels are located at a determined distance from each other, so as to keep the guide wires apart when they are inserted and passed through the first tissue portion. Preferably, the second operative channel 70 is located opposite the visualization device 64 relative to the first operative channel 66.

In accordance with a possible embodiment, the connecting head 68 is suitable for being interference-fitted on a distal end of the visualization device 64. For example, the connecting head 68 comprises elastic tabs 72 which extend from a proximal end of the head.

In accordance with an alternative embodiment, the insertion device has an individual operative channel in order to insert the guide wires simultaneously and placed beside one to the other. In this case, the guide wires pass through the first tissue portion at a same opening. Optionally, the two guide wires can be originally connected to each other at the distal end and, subsequently, separated at the end of their insertion.

Figure 2:
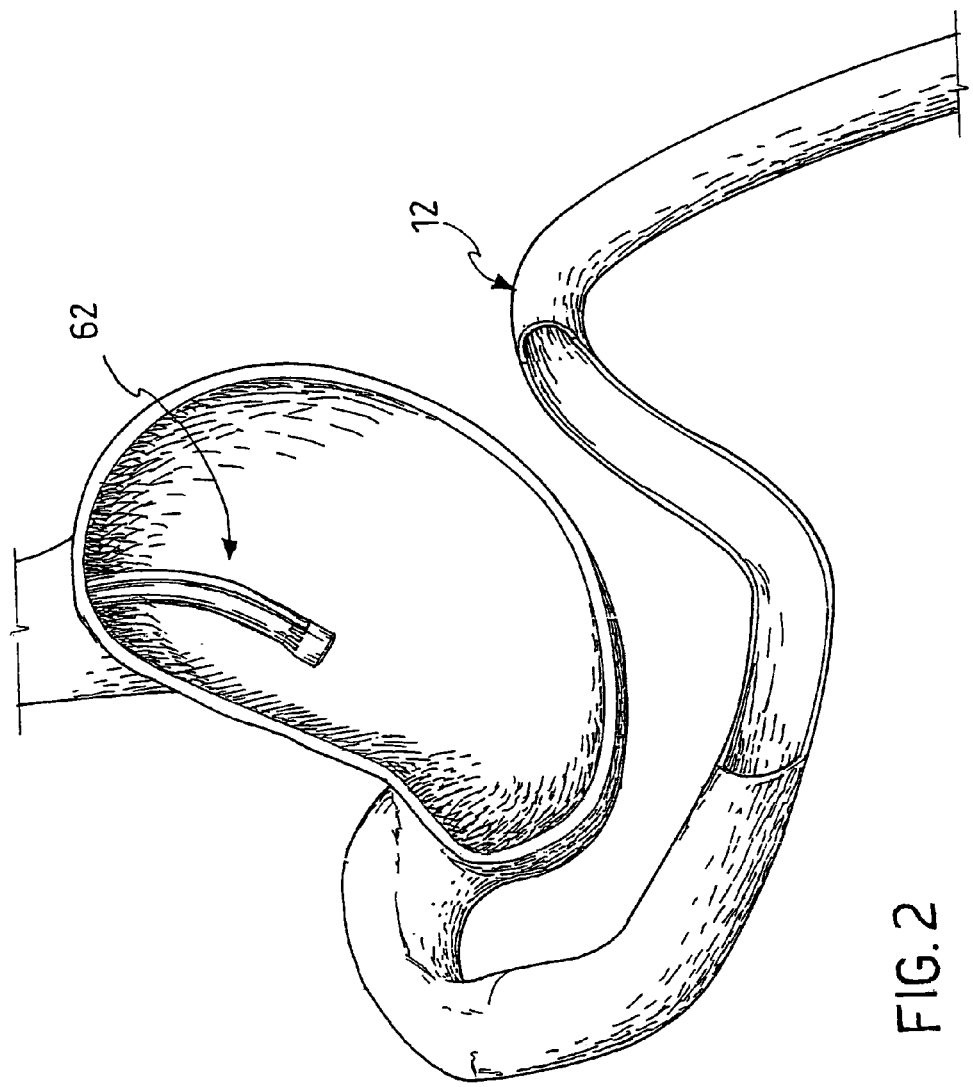
FIG. 2 illustrates a step of a method for performing anastomoses in tracts of the digestive tube carried out on the portion of FIG. 1.
Figure 3:
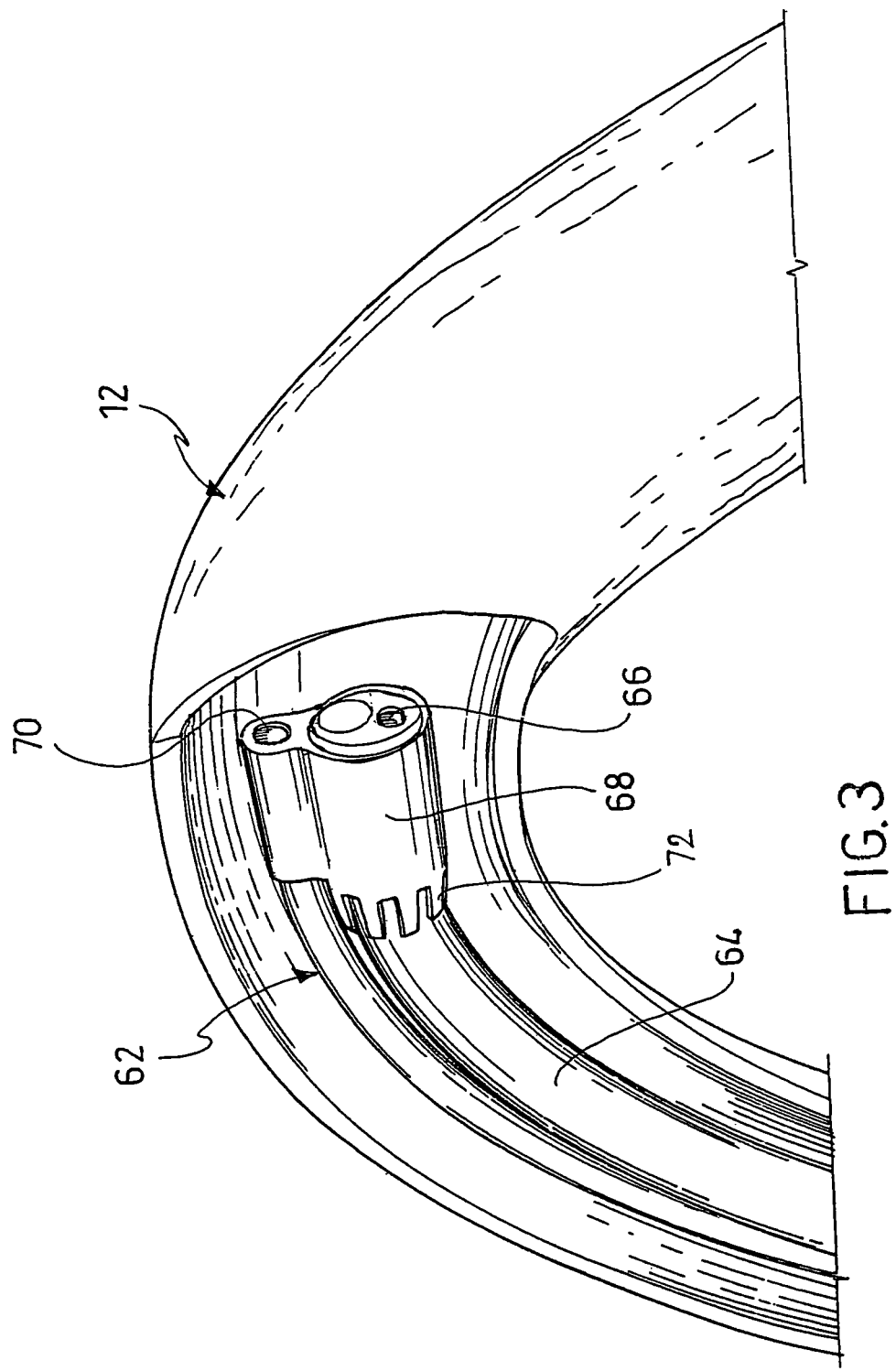
FIGS. 3 to 6 illustrate perspective and enlarged views of a detail from FIG. 1 corresponding to further steps of the method, respectively.

The insertion device 62 is assembled externally to the patient, by inserting the connecting head 68 on the distal end of the elongated structure (visualization device 64—FIG. 31). Subsequently, the insertion device 62 is introduced in the oesophagus and in the stomach (FIG. 2) to the jejune and the first tissue portion 12 (FIG. 3).

Figure 4:
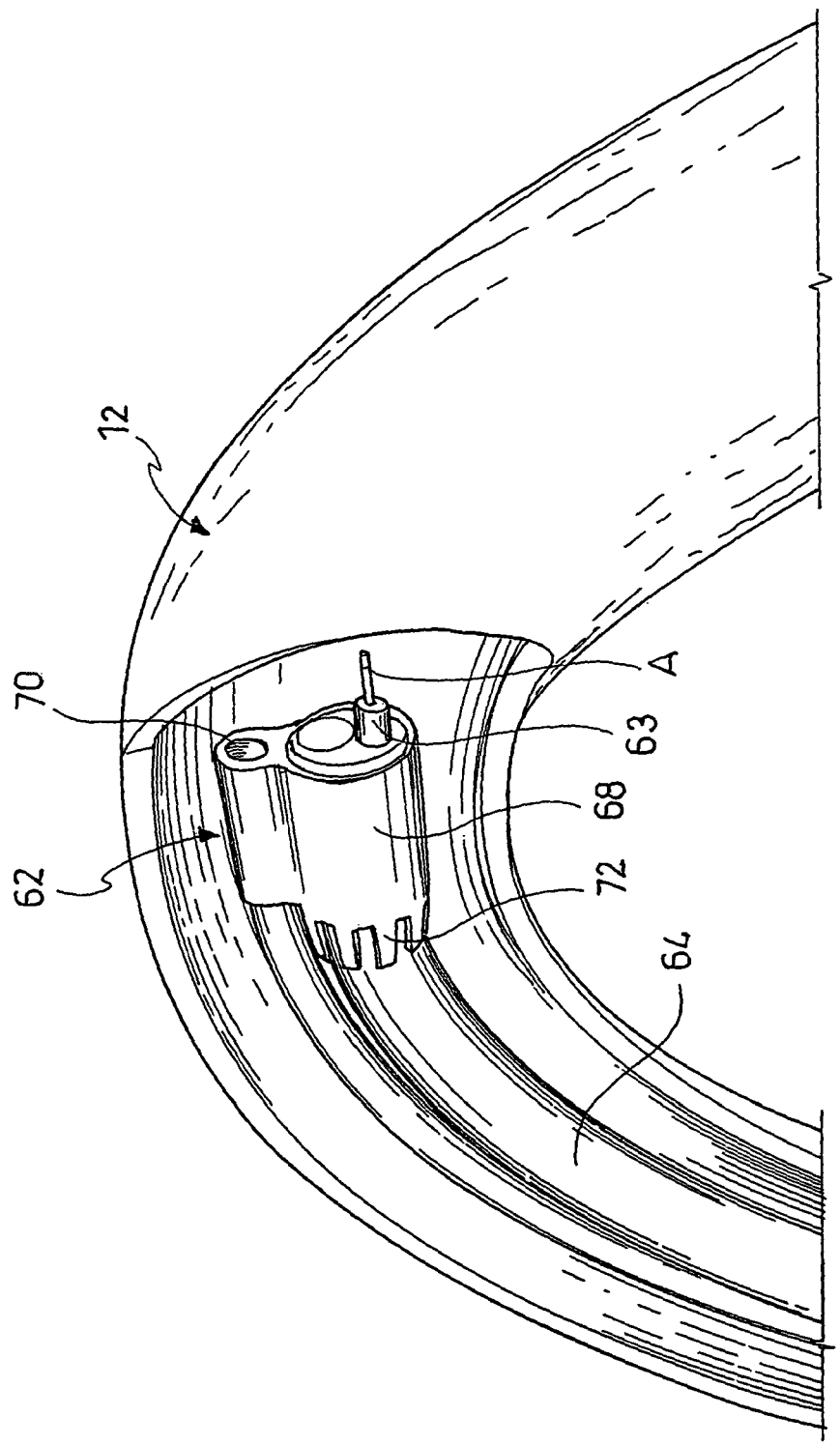
Figure 5:
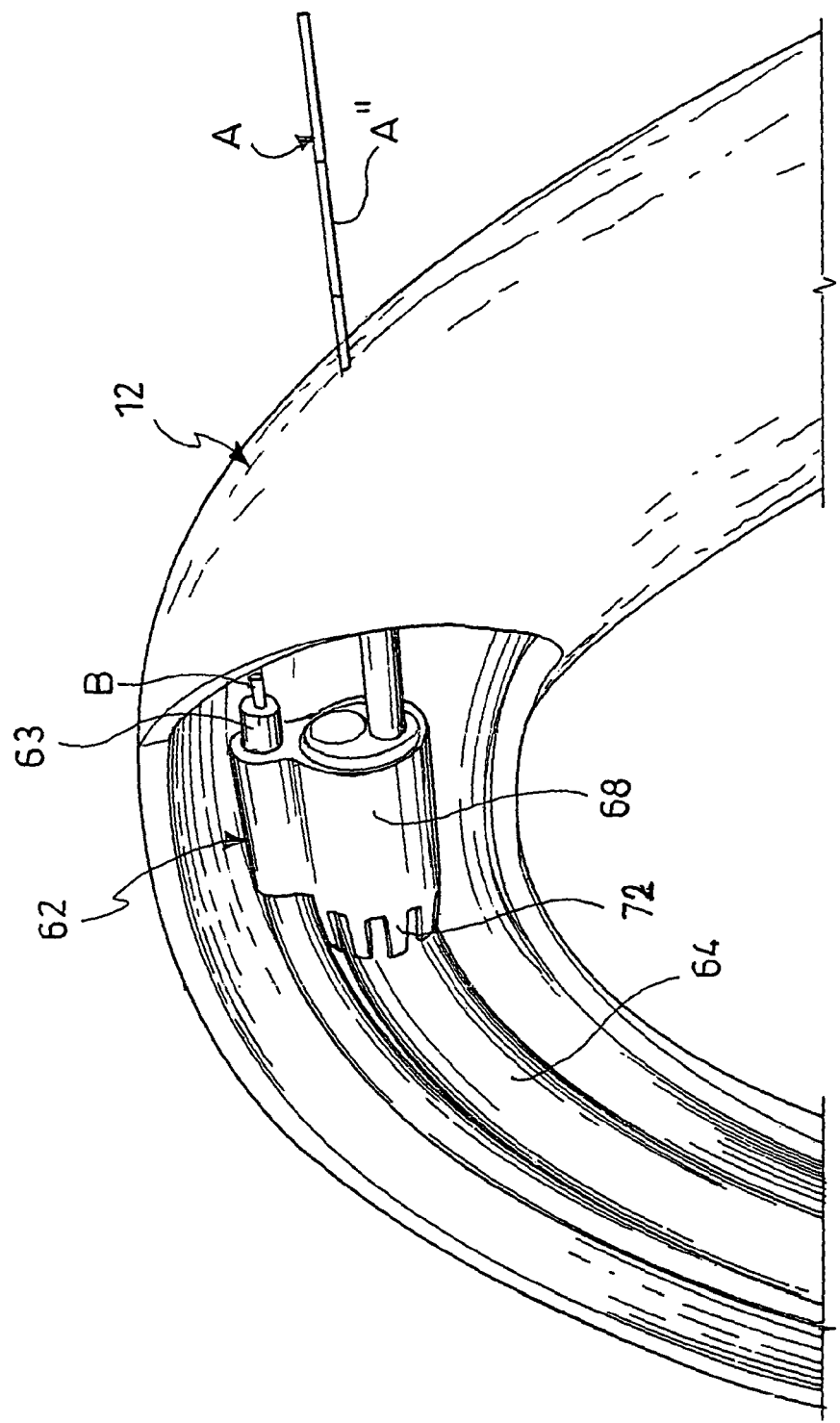
Figure 6:
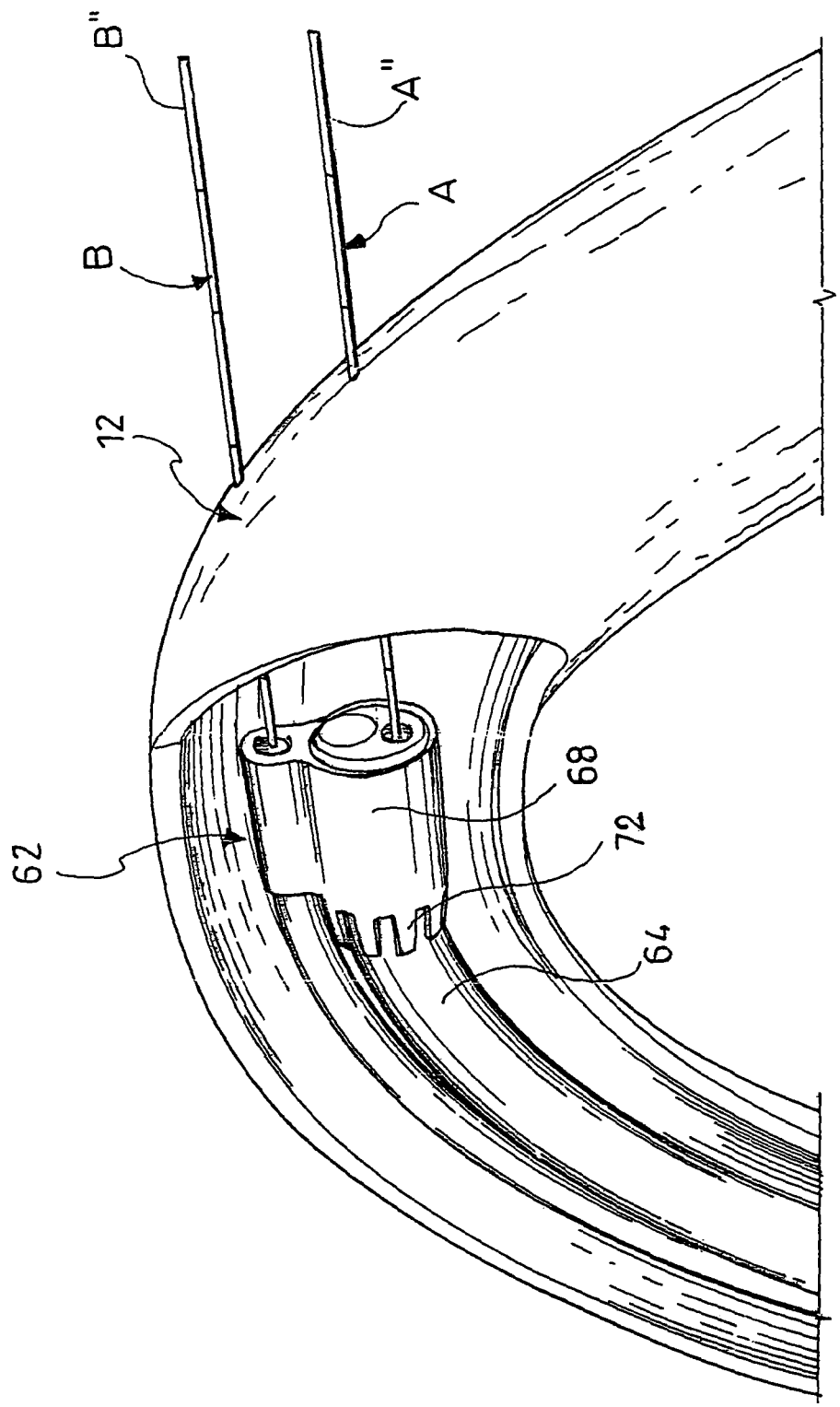
Figure 7:
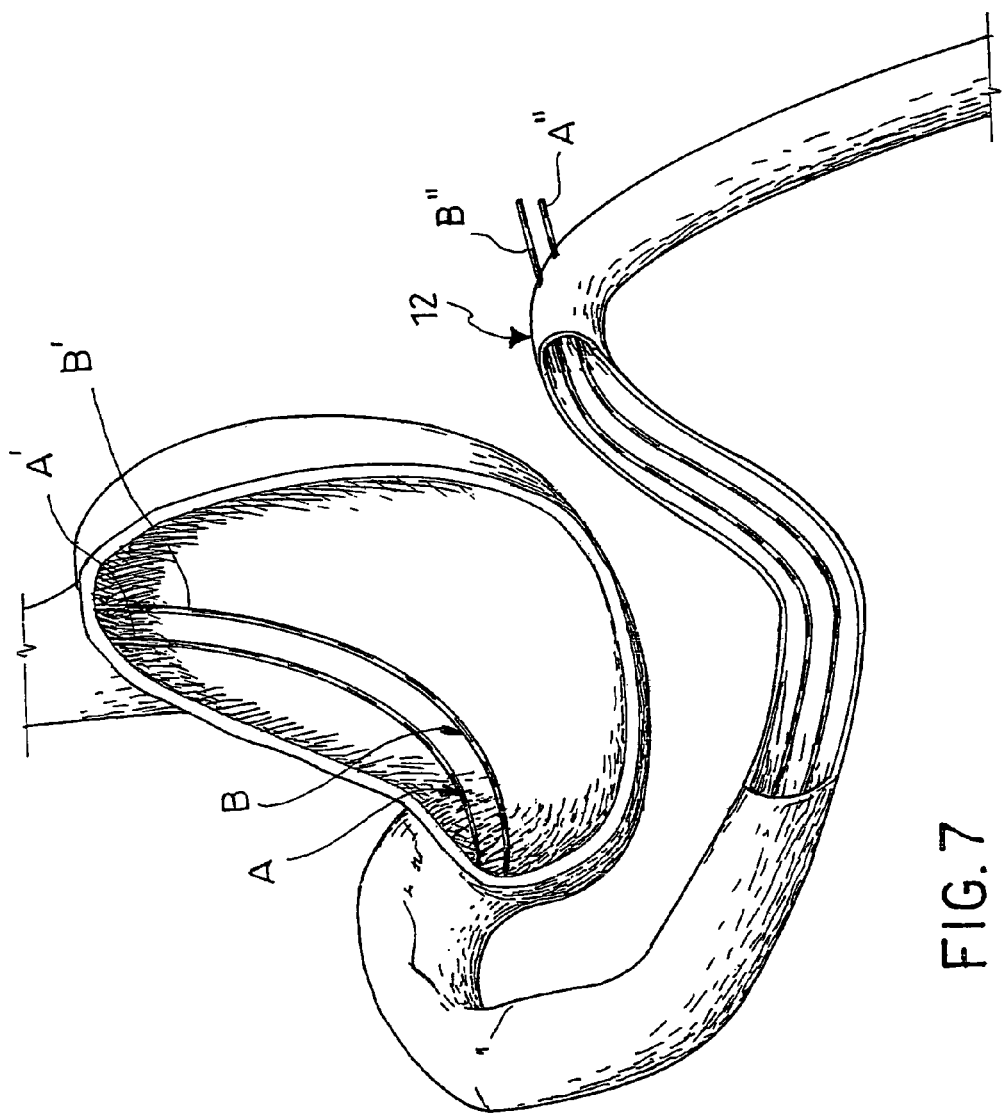
FIG. 7 illustrates the perspective and partially sectional view of FIG. 1 at the end of a first sequence of steps.

A guide wire A is inserted through the first operative channel 66 until a distal end of the guide wire projects from the distal end of the insertion device 62 (FIG. 4) and passes through the wall of the first tissue portion. A distal end portion A" of the guide wire extends beyond the wall of the first tissue portion. Furthermore, a second guide wire is inserted through the second operative channel 70 until a distal end of the guide wire projects from the distal end of the insertion device 62 (FIG. 5) and passes through the wall of the first tissue portion. A distal end portion B" of the second guide wire extends beyond the wall of the first tissue portion (FIG. 6). The insertion device is then withdrawn (FIG. 7).

Before introducing the guide wires, the first tissue portion wall is punched for example by means of radiofrequency or via other devices, optionally introduced by means of the same insertion device 62. For example, a sheath 63 containing a radiofrequency needle is inserted along the first operative channel 66 to the first tissue portion wall. The radiofrequency needle punches the wall, and subsequently a guide wire A is inserted along the sheath 63 until passing through the first tissue portion wall, at the hole made by the radiofrequency needle. The same procedure can be followed when the guide wire B is positioned through the second operative channel 70.

In accordance with a different embodiment and application, when the guide wires are inserted, they are drawn together and placed beside one to the other through only one individual operative channel, for example of an insertion device or of a visualization device. Before introducing the guide wires, the first tissue portion wall is punched in an individual point, for example by means of radiofrequency or through other devices, optionally introduced by means of the same insertion device.

In the case as illustrated in the figures, the first tissue portion substantially corresponds to a tract of the jejune, and the guide wires pass therethrough after a jejunostomy has been performed.

Figure 8:
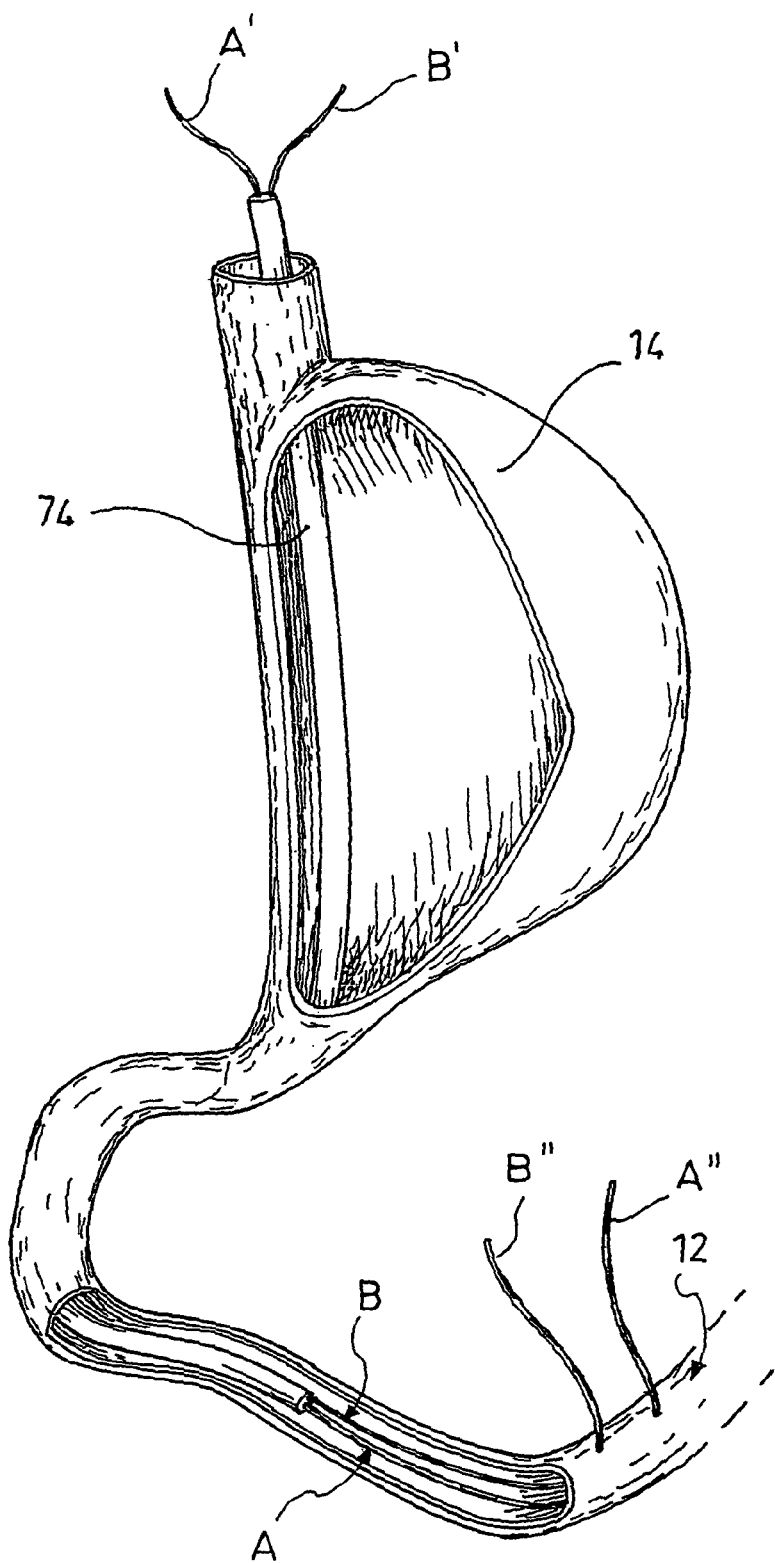
FIG. 8 illustrates the perspective and partially sectional view of FIG. 7 according to a possible variation of the method.
Figure 9:
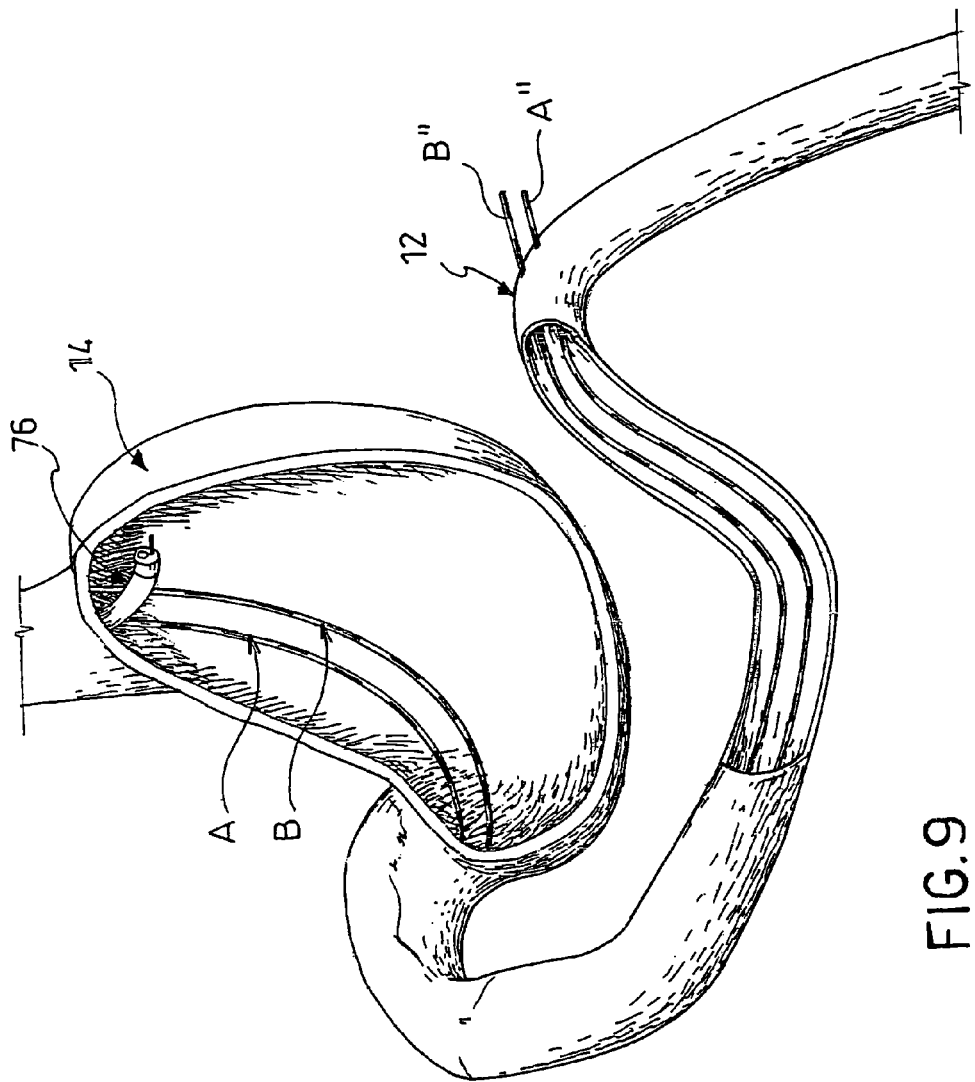
FIG. 9 illustrates a further step of the method carried out on the portion of FIG. 7.

Optionally, preferably before passing through the second tissue portion, a step is provided of separating and identifying the proximal end portions A' and B' of the guide wires coming out of the luminal structure. Preferably, the step of separating and identifying the proximal end portions of the guide wires coming out of the luminal structure is performed by introducing a first sheath 74 on the two guide wires starting from a proximal end of the guide wires. The first sheath has a characterizing element, for example it is made in a certain colour (FIG. 8).

Figure 10:
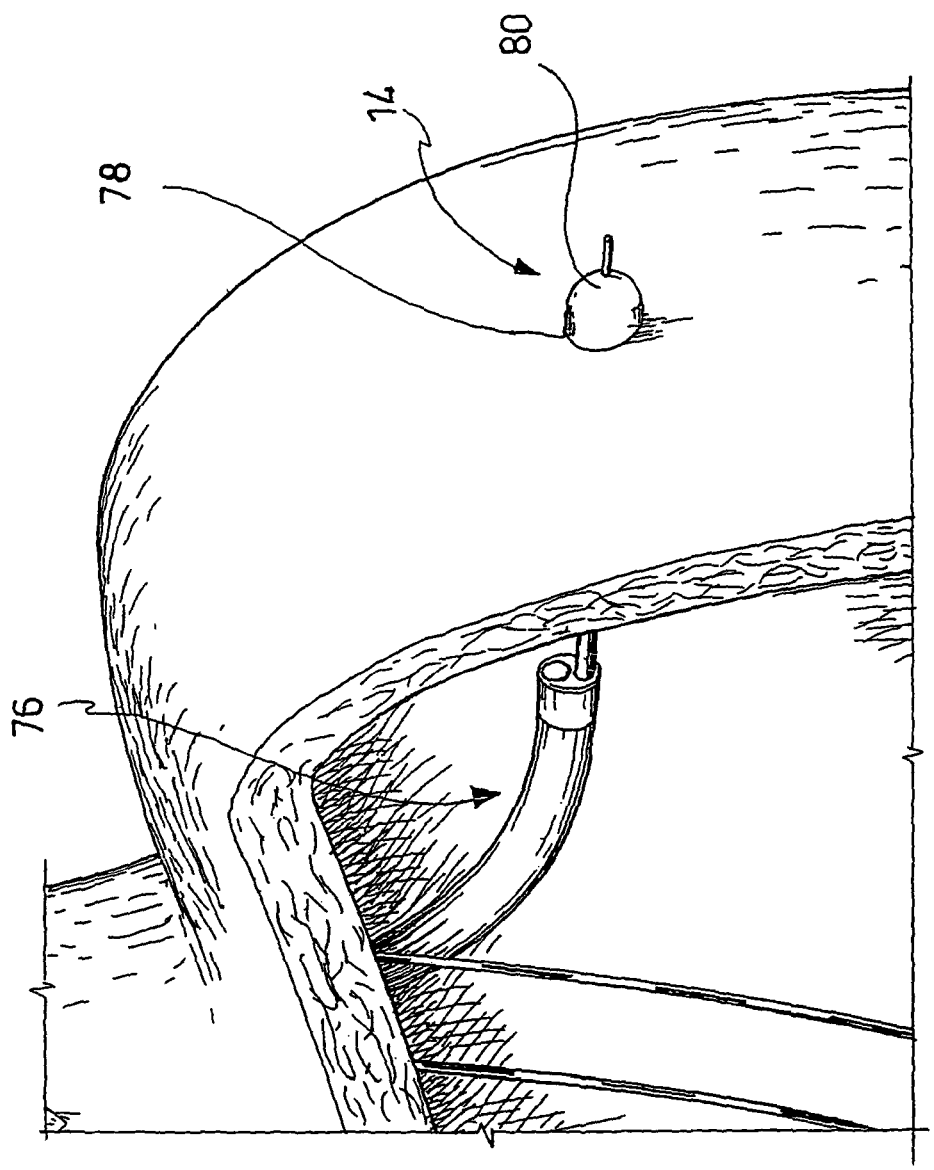
FIGS. 10-11 illustrate perspective and enlarged views of a detail from FIG. 7 corresponding to further steps of the method, respectively.
Figure 11:
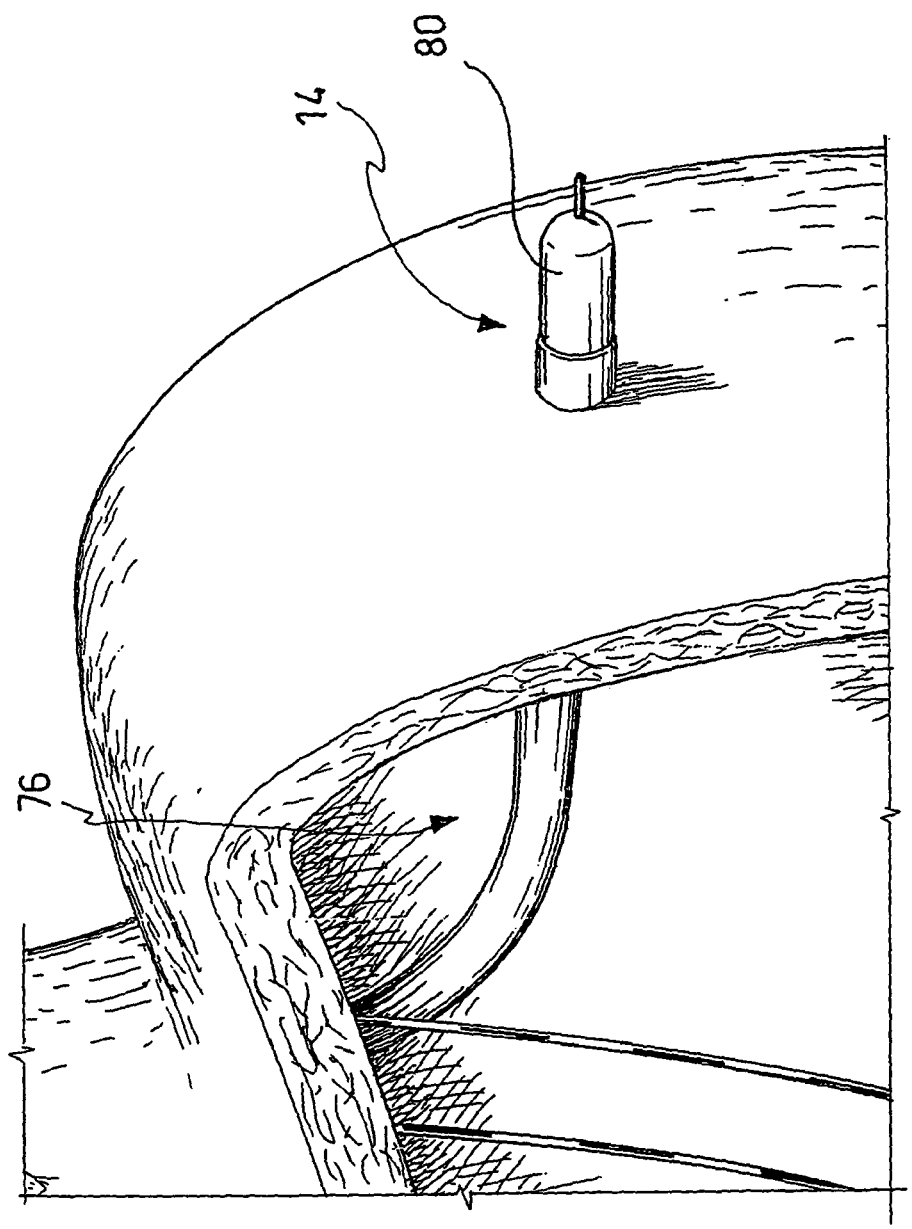
Figure 12:
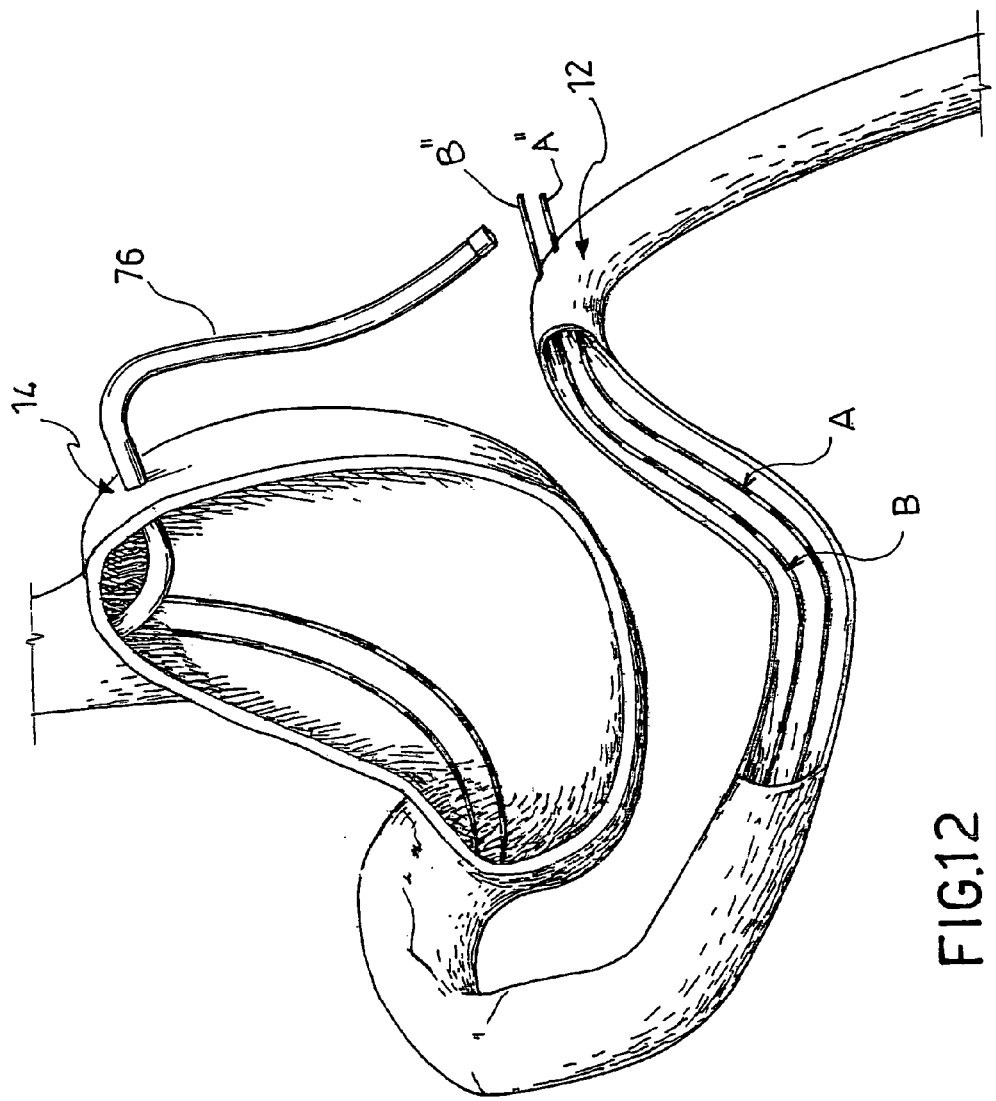
FIG. 12 illustrates a further step of the method carried out on the portion of FIG. 7.
Figure 13:
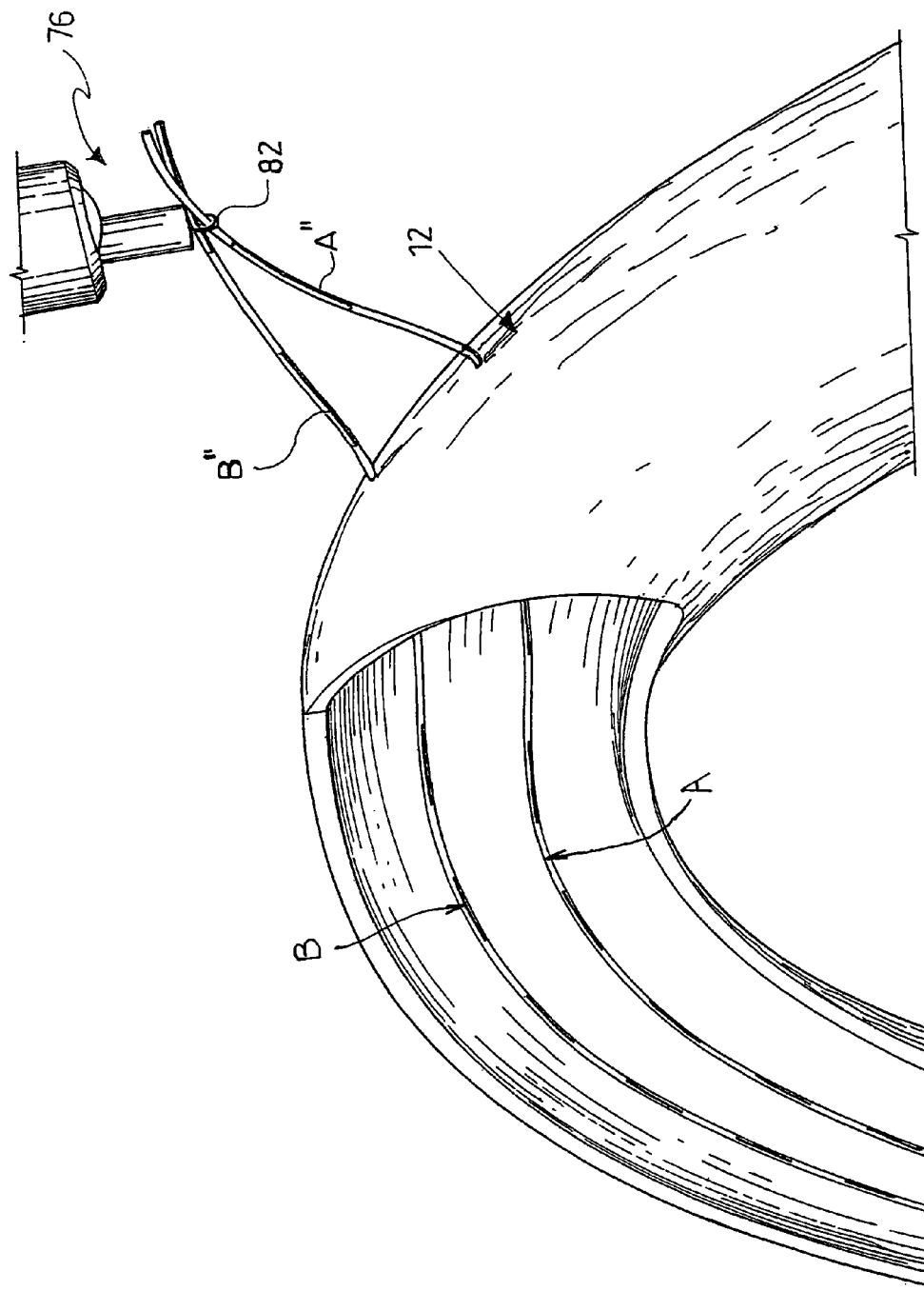
FIG. 13 illustrates a perspective and enlarged view of a detail from FIG. 12 corresponding to a further step of the method.
Figure 14:
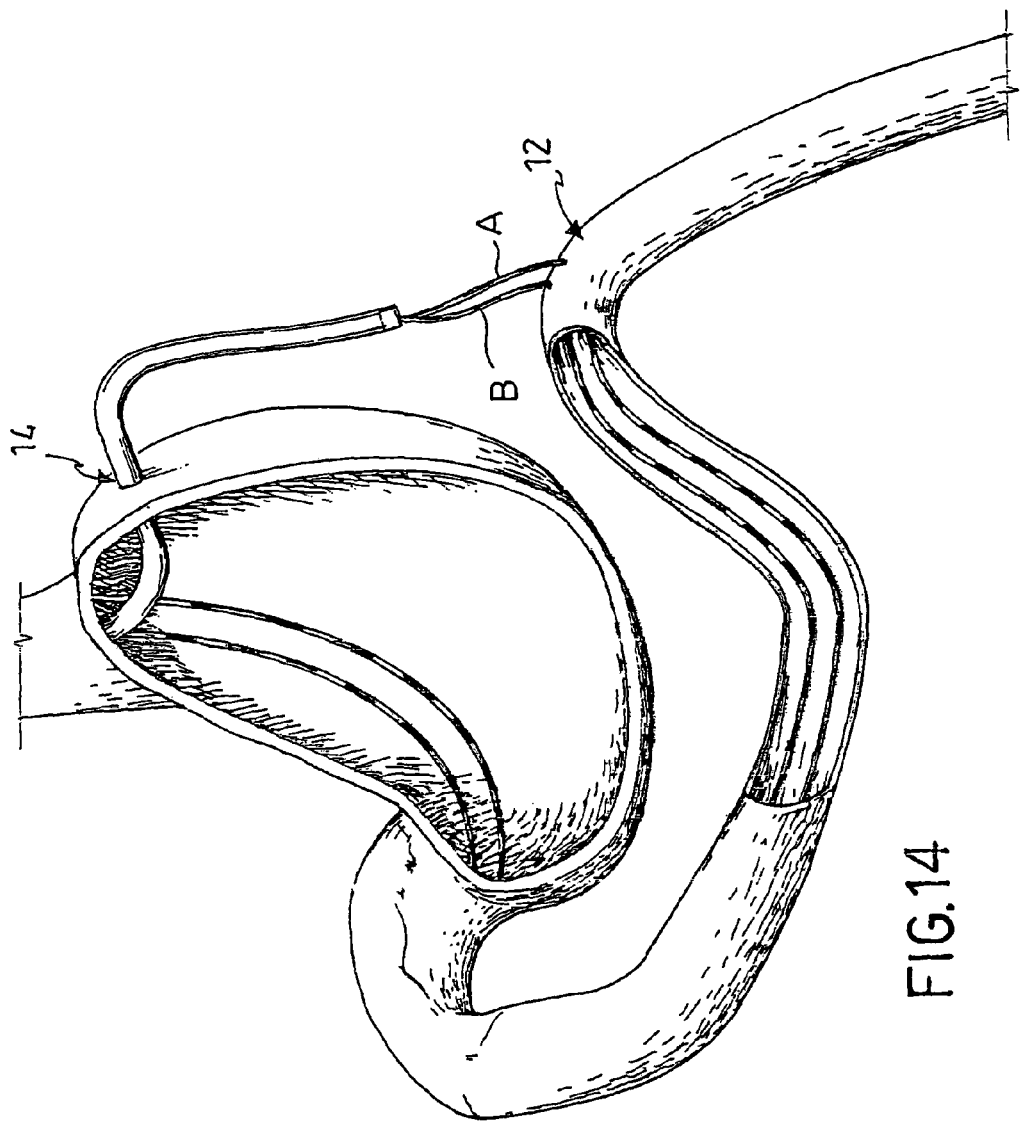
FIG. 14 illustrates a further step of the method carried out on the portion of FIG. 7.
Figure 15:
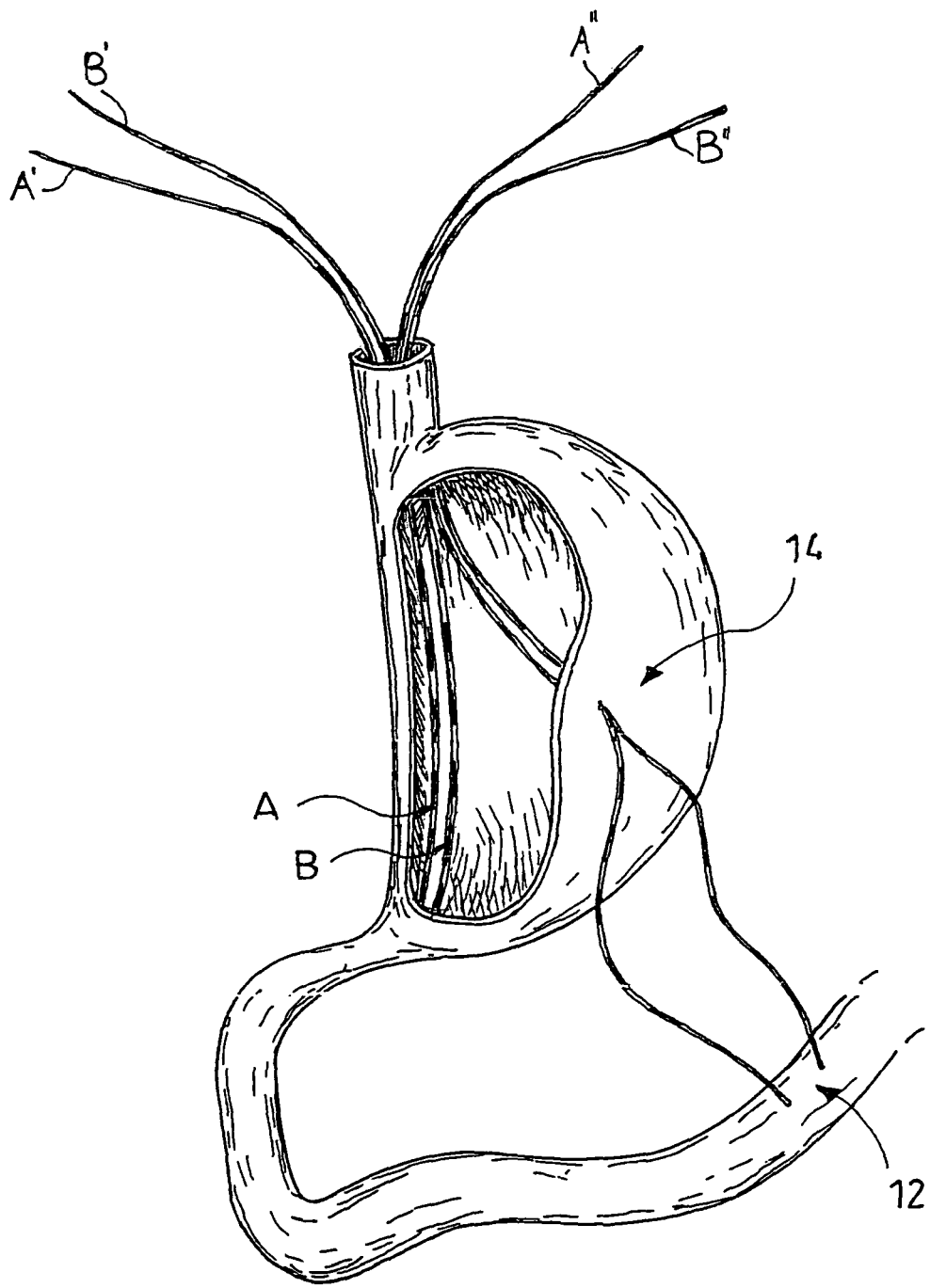
FIG. 15 illustrates the perspective and partially sectional view of FIG. 7 at the end of a second sequence of steps of the method.

To complete the loop, the insertion of a grasping device 76 through the second tissue portion 14 to be connected in order to grasp the distal end portions A" and B" of the two guide wires is advantageously provided. In order to make the grasping device pass through the second tissue portion, the creation of a hole 78 (gastrostomy with reference to the figures) is advantageously provided in the second tissue portion 14, for example by means of a radiofrequency needle or the like. The hole 78 is optionally enlarged by a balloon catheter 80, preferably introduced via an operative channel of the grasping device (FIGS. 10 and 11). In accordance with a possible embodiment, the grasping device comprises a visualization device, for example of the gastroscopic kind, in which an operative channel is used to insert the balloon catheter 80 and subsequently a snare 82 for grasping the distal end portions A" and B" of the guide wires. The grasping device 76 passes through the hole 78 and reaches the distal ends of the guide wires (FIG. 12). When the snare closes on the distal end portions of the guide wires (FIG. 13), the snare, together with the grasping device, is retracted through the hole 78 (FIG. 14) to the orifice through which it had been introduced. The guide wires are then located to form a loop with distal and proximal end portions preferably brought back in the same orifice (FIG. 15).

The grasping device can be activated in a wholly endoluminal way, or through laparoscopic supervision. According to this alternative, not shown, the hole 78 (gastrostomy) is not enlarged and only the loop is passed therethrough. Subsequently, the surgeon laparoscopically individuates the distal end portions A" and B" and inserts them into the snare, under laparoscopic control. Finally, the snare is closed again and dragged back so as to form the loop, as provided in FIG. 15.

Figure 16:
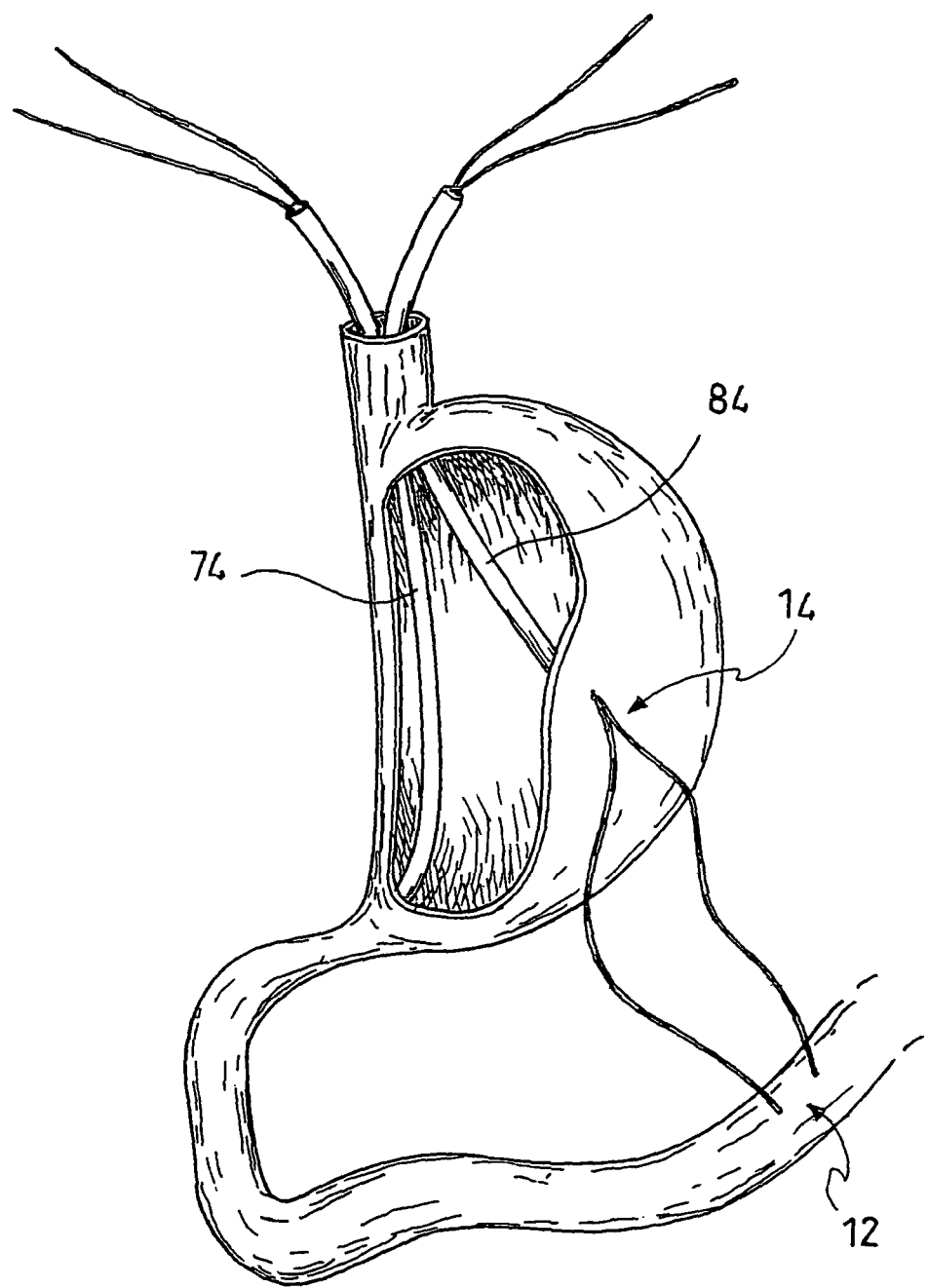
FIG. 16 illustrates the perspective and partially sectional view of FIG. 8 according to a possible variation of the method.

Optionally, a step is provided of separating and identifying the distal end portions of the guide wires that come out of the luminal structure after they have passed through the first and second tissue portions. Advantageously, this step of separating and identifying the distal end portions of the guide wires is performed by introducing a second sheath 84 on the two guide wires starting from the distal end of the guide wires. The second sheath has a characterizing feature, for example a colour other than that of the first sheath 74 (FIG. 16).

Once the loop has been formed, the anastomotic device is inserted on the two guide wires so as to draw and optionally keep drawn the first tissue portion and the second tissue portion together, as described above. Optionally, the abutment portion 18 is pre-associated or integral to the guide wires in such a way that when the distal ends of the guide wires are dragged, the abutment portion is dragged and drawn together to the tissue portions to be connected.

In the case where the distal end portions of the guide wires are connected, it is possible to divide them after forming the loop, or subsequently to the formation of the same.

In the case where the first sheath 74 is provided, the abutment portion 18 of the anastomotic device 10 is inserted on the proximal end portions of the guide wires after removing the first sheath 74 which, when the abutment portion of the anastomotic device has drawn the two tissue portions to be connected together, is preferably repositioned on the proximal end portions of the guide wires.

In the case where a second sheath 84 is provided, the locking portion 20 of the anastomotic device 10 is subsequently inserted on the distal end portions A" and B" of the guide wires after removing the second sheath 84.

The final step of the method provides for the completion of the anastomosis. Using the anastomotic device as described above, the anastomosis is performed at the opening of the two annular structures of the anastomotic device.

Referring to the application described in the annexed Figures, in accordance with a preferred embodiment the anastomosis is performed on the side of the jejune, by introducing for example a radiofrequency needle suitable for punching the wall. Optionally, a balloon catheter is then introduced to enlarge the punching and/or a further tool to remove a part of the tissue. In accordance with an alternative embodiment, the anastomosis can be performed on the side of the stomach. In this case, it is possible to provide the introduction of a shielding device in the jejune, in order to avoid that the punching also affects the jejune wall opposite to that in which the anastomosis has to be performed.

Finally, the guide means (guide wires) are removed, for example by pulling the proximal end portions A' and B', as in the case where the locking members 61 are provided. In other terms, the guide wires are pulled in the direction in which they can slide relative to the anastomotic device. Optionally, a seal test of the anastomosis based on methylene blue can be provided.

With reference to the annexed Figures, the aforesaid method can be used for example during a step of performing a gastro-jejuneanastomosis (G-J), advantageously endoluminally. In fact, FIG. 1 illustrates a portion of the digestive apparatus comprising the oesophagus, the stomach and a tract of the intestine corresponding to the jejune. The two guide wires A and B are introduced through the oesophagus, which is a natural orifice, or through another orifice, also artificial, until reaching the stomach and a tract of the jejune (FIG. 7). Subsequently, the two guide wires A and B are loop-shaped with distal A", B" and proximal end portions A', B' debouching through the aforesaid orifice (FIG. 15). The loop passes through the portions to be connected, respectively a jejunectomy and a gastrostomy.

Particularly, the two guide wires A and B are introduced through the oesophagus, the stomach and a tract of the jejune and one distal end thereof is passed through the jejune wall corresponding to the first tissue portion to be connected (FIG. 6), for example after punching this wall by means of radiofrequency needles as described above. This step is performed preferably via an insertion device 62 as illustrated in FIGS. 2-6, as described above. In accordance with a different embodiment and application, the guide wires are inserted by being drawn together and placed beside one to the other through a single operative channel, for example of an insertion device or of a visualization device. Before introducing the guide wires, the first tissue portion wall is punched in an individual point, for example by means of radiofrequency or through other devices, optionally introduced by means of the same insertion device.

In the case where the aforesaid method is a part of a gastro-intestinal by-pass procedure, it will be then possible to proceed to the performing of a further entero-enteroanastomosis (for example a jejuno-jejuno- or an ileum-jejunoanastomosis), optionally by repeating the steps described above.

The method may be optionally performed also using an individual guide wire when using an anastomotic device suitable to the purpose.

Such as described in the broadest embodiment thereof, or in the specific application to perform a gastro-jejunoanastomosis (G-J), the aforesaid method allows a continuous control both in the step of positioning the guide wires and in the step of drawing together and connecting the tissue portions. The steps provided herein further allow an endoluminal approach for procedures until now applied in the conventional surgery or laparoscopically, even if laparoscopic or partially laparoscopic techniques are not excluded.

The above-described method can be further used to perform different kinds of anastomoses, for example a jejuno-jejunoanastomosis, particularly in order to achieve a gastro-intestinal by-pass, or a colon-colon anastomosis with transanal access.

Figure 35:
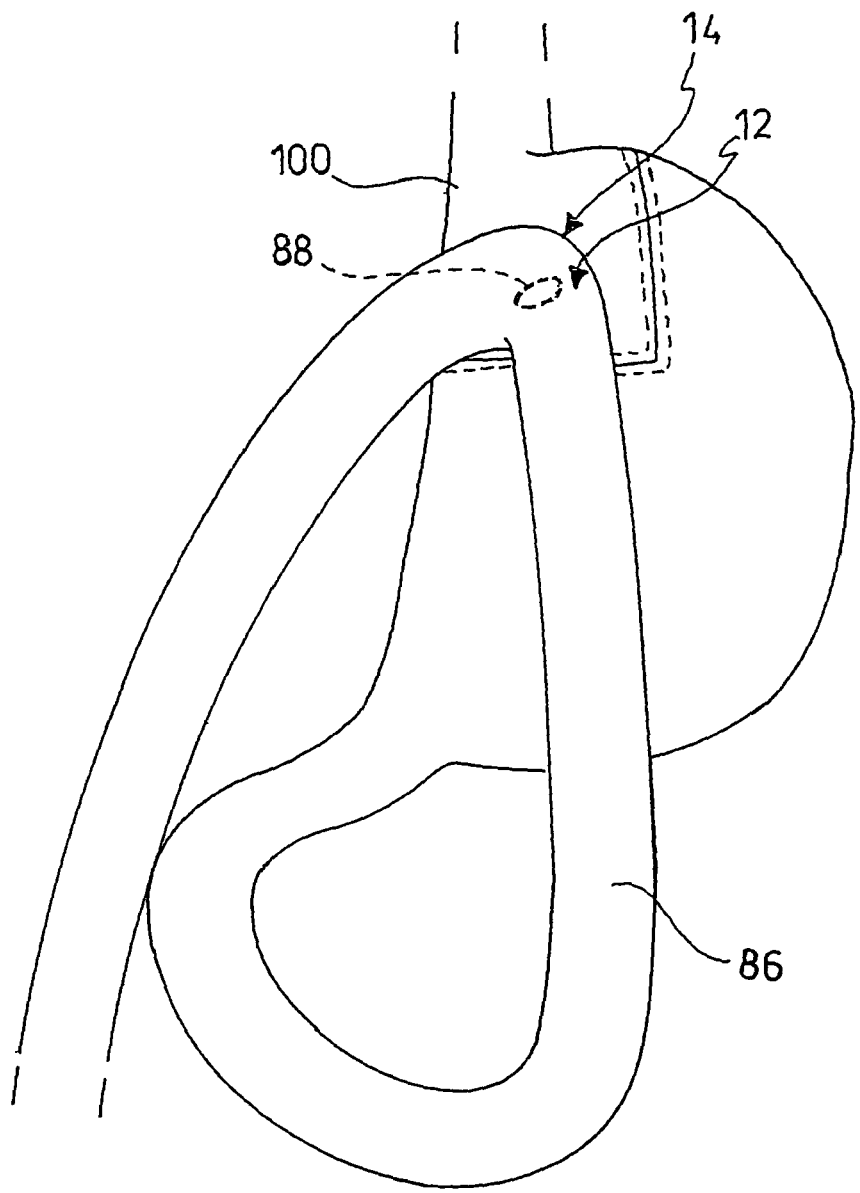
FIGS. 35 and 36 illustrate two corresponding steps of a possible embodiment of a method for performing anastomoses in tracts of the digestive tube.
Figure 36:
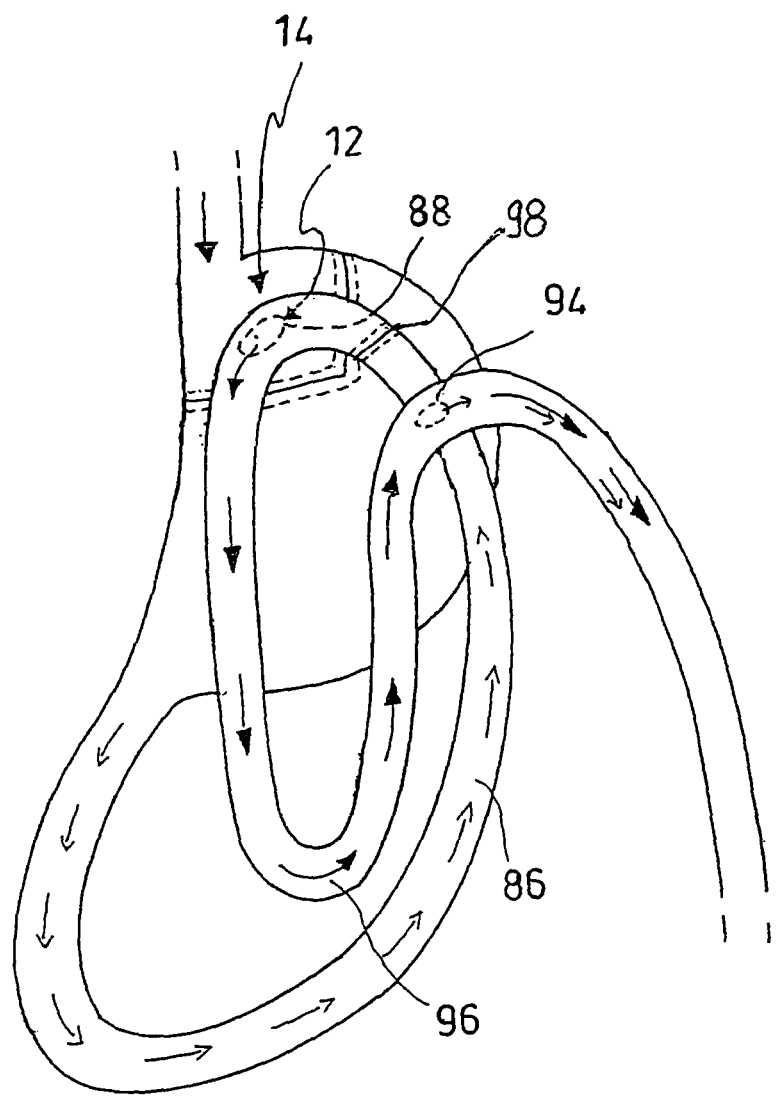

In accordance with a possible embodiment, the aforesaid method to perform anastomosis in tracts of the digestive tube can be applied in the case illustrated in FIGS. 35 and 36, in particular to obtain a gastro-intestinal by-pass. This method comprises steps of drawing-together and connecting the tissues 12, 14 to form anastomoses 88, 94 suitable for keeping or reintegrating the integrity and the continuity of the intestinal duct after each formation of an anastomosis (both the gastro-jejuno anastomosis and the jejuno-jejuno anastomosis). Furthermore, the gastro-jejuno anastomosis and the jejuno-jejuno anastomosis are performed at a closed-up distance, thus allowing for a wide operative and visual field, while remaining only in the upper area of the abdomen.

In this case also, the steps of bringing tissues together and creating the gastro-jejunoanastomosis and/or the jejuno-jejunoanastomosis can be performed using a guide means comprising preferably at least two guide wires that are placed side by side and located to form a loop which passes through the tissue portions to be connected. The guide means can be associated to an anastomotic device according to the present invention or other anastomotic or positioning devices. The aforesaid method can be performed endoluminally, or in a partially or wholly laparoscopic way.

In all the cases provided, the partial creation of a pocket 100 into the stomach can be preventively provided, to which the first portion of the jejune will be connected.

With reference to FIGS. 35 and 36, subsequently a first guide wire loop is made through the open portion of the gastric pocket and through the portions of the jejune and the stomach to be connected. An anastomotic device is inserted and locked on the guide means and dragged, by the guide means, until abutting against the first portion to be connected and drawing it together with the second portion to be connected. This first sequence of steps ends by carrying out a gastro-jejunoanastomosis 88 and forming a first intestine loop 86.

Subsequently, a guide wire second loop is made through the open portion of the gastric pocket and through the two portions of the jejune to be connected.

Also in this case, an anastomotic device is inserted and locked in a direction on the guide means and dragged, by means of the same guide means, until abutting against the first portion to be connected and drawing it together with the second portion to be connected. This second sequence of steps ends by performing an entero-enteroanastomosis 94, carrying out a second ring 96 of intestine and completing the gastric pocket 100. A section line of the intestine between the two anastomoses has been designated with 98.

The passing of the guide means through the walls of the tissues to be connected can be performed by punching the wall (for example with radiofrequency needles) at the area intended to form the anastomosis, so as that after the formation of the anastomosis, the continuity of the intestinal duct is reintegrated.

An anastomotic device suitable to the purpose can be that described in the present application, or anastomotic or positioning devices suitable for releasing an anastomotic ring to perform the anastomosis, or a circular stapler sliding on the guide means and cooperating with an anvil, also sliding on the guide means.

In accordance with a possible embodiment, the guide means and the anastomotic device (particularly an abutment portion 18) can be spaced apart from each other and suitable for being mutually associated upon use. Or, a guide means can be provided in which the anastomotic device (and particularly the abutment portion 18) is pre-assembled or integrated on the guide means, so as it can be dragged in a direction and taken off in the opposite direction or be taken off together with the guide wires.

Furthermore, during insertion, when at least two guide wires are provided, the guide wires can be at least partially placed side by side at a certain distance from each other, or placed beside and drawn together. In this case, by providing an insertion device, the guide wires can be introduced by means of a same operative channel, placed side by side and drawn together, so as to pass through the first tissue portion at a common opening. Optionally, during this step, the distal ends of the guide wires can be mutually connected. They will be optionally separated after the loop has been made.

As in the previous case, this method allows to reduce the mortality risks in the case of gastro-intestinal by-passes and to considerably minimize the intervention times. The preservation of the continuity of the intestine until the completion of the two anastomoses allows for the simultaneous assessment of both. Furthermore, by virtue of the close arrangement of the two anastomoses, the surgical field is restricted to the upper area of the abdomen.

To the preferred embodiments of the devices and methods above described, those skilled in the art, aiming at meeting contingent and specific needs, will be able to bring a number of modifications, adaptations and replacements of elements with other functionally equivalent, without however departing from the scope of the following claims.

The invention claimed is:

1. A positioning device for deploying at least one locking portion (20) of an anastomotic device (10) for approximating a first tissue portion (12) and a second tissue portion (14) to be connected by means of anastomosis, said positioning device comprising:
   an elongated structure (50) having a distal end,
   a head (52) adapted to be interference-fitted on the distal end of the elongated structure (50), said head (52) having:
      a distal end defining a thrust surface (58) for engaging said locking portion (20) of the anastomotic device (10), at least two channels (56), each of said two channels (56) adapted to slidingly receive a guide wire (A, B), respectively, wherein said two channels (56) are arranged on opposite sides of said head (52) such that when the head (52) is interference-fitted on the distal end of the elongated structure (50), the entire positioning device can slide along said guide wire (A,B) received by said channel (56).

2. The positioning device according to claim 1, wherein said head (52) comprises elastic tabs (54) for said interference fit with the elongate structure (50), said elastic tabs (54) extending from a proximal end of the head opposite the thrust surface (58).

3. The positioning device according to claim 1, wherein said distal end of the head (52) is counter-shaped relative to said locking portion of the anastomotic device (10).

4. The positioning device according to claim 1, wherein said distal end of the head (52) comprises at least one opening (60) for receiving elastic tabs (28) of the locking portion (20).

5. The positioning device according to claim 1, wherein said elongated structure is a flexible structure.

6. The positioning device according to claim 1, wherein said elongated structure is a flexible structure suitable for becoming rigid.

* * * * *